(12) United States Patent
Bartus et al.

(10) Patent No.: US 6,613,308 B2
(45) Date of Patent: Sep. 2, 2003

(54) PULMONARY DELIVERY IN TREATING DISORDERS OF THE CENTRAL NERVOUS SYSTEM

(75) Inventors: Raymond T. Bartus, Sudbury, MA (US); Dwaine F. Emerich, Cranston, RI (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 0 days.

(21) Appl. No.: 09/877,734

(22) Filed: Jun. 8, 2001

(65) Prior Publication Data

US 2002/0058009 A1 May 16, 2002

Related U.S. Application Data

(63) Continuation-in-part of application No. 09/665,252, filed on Sep. 19, 2000, now Pat. No. 6,514,482.

(51) Int. Cl.[7] .............................. A61K 9/12; A61K 9/14; A61K 9/72
(52) U.S. Cl. .......................... 424/45; 424/46; 424/489; 128/203.15; 514/220; 514/252; 514/567; 560/43
(58) Field of Search .................... 424/45, 489, 46; 514/220, 252, 567; 128/203.15; 560/43

(56) References Cited

U.S. PATENT DOCUMENTS

| | | | |
|---|---|---|---|
| 4,814,161 A | 3/1989 | Jinks et al. ................ 424/45 |
| 4,895,719 A | 1/1990 | Radhakrishnan et al. ...... 424/45 |
| 5,118,494 A | 6/1992 | Schultz et al. ............... 424/45 |
| 5,166,202 A | 11/1992 | Schweizer ................... 514/220 |
| 5,284,133 A | 2/1994 | Burns et al. ............ 128/200.23 |
| 5,354,885 A * | 10/1994 | Milman et al. ............... 560/43 |
| 5,457,100 A | 10/1995 | Daniel ........................ 514/220 |
| 5,510,350 A | 4/1996 | Oxford et al. .............. 514/252 |
| 5,654,007 A | 8/1997 | Johnson et al. ............. 424/489 |
| 5,756,071 A | 5/1998 | Mattern et al. ............... 424/45 |
| 5,855,913 A | 1/1999 | Hanes et al. ................ 424/489 |
| 5,874,064 A | 2/1999 | Edwards et al. .............. 424/46 |
| 5,875,776 A | 3/1999 | Vaghefi ................. 128/203.15 |
| 5,922,354 A | 7/1999 | Johnson et al. ............. 424/489 |
| 5,981,474 A | 11/1999 | Manning et al. ............... 514/2 |
| 5,985,309 A | 11/1999 | Edwards et al. ............ 424/426 |
| 6,019,968 A | 2/2000 | Platz et al. .............. 424/130.1 |
| 6,048,857 A | 4/2000 | Ellinwood, Jr. et al. ..... 514/221 |
| 6,103,270 A | 8/2000 | Johnson et al. ............. 424/489 |
| 6,136,295 A | 10/2000 | Edwards et al. ............... 424/45 |
| 6,165,463 A | 12/2000 | Platz et al. .............. 424/130.1 |
| 2002/0035993 A1 * | 3/2002 | Edwards et al. ........ 128/203.15 |

FOREIGN PATENT DOCUMENTS

| | | |
|---|---|---|
| CA | 2152684 | 6/1995 |
| EP | 0496 307 A1 | 7/1992 |
| JP | 61022019 | 1/1986 |
| WO | WO 91/16882 | 11/1991 |
| WO | WO 98/31346 | 7/1998 |
| WO | WO 98/46245 | 10/1998 |
| WO | WO 00/72827 A3 | 12/2000 |
| WO | WO 01/95874 A2 | 12/2001 |

* cited by examiner

*Primary Examiner*—Michael G. Hartley
*Assistant Examiner*—M. Haghighatian
(74) *Attorney, Agent, or Firm*—Hamilton, Brook, Smith & Reynolds, P.C.

(57) ABSTRACT

A method for treating a disorder of the central nervous system includes administering to the respiratory tract of a patient a drug which is delivered to the pulmonary system, for instance to the alveoli or the deep lung. The drug is administered at a dose which is at least about two-fold less than the dose required by oral administration. Particles that include the drug can be employed. Preferred particles have a tap density of less than about 0.4 g/cm³. In addition to the medicament, the particles can include other materials such as, for example, phospholipids, amino acids, combinations thereof and others.

24 Claims, 19 Drawing Sheets

Alprazolam Dose (mgs)

PULMONARY DELIVERY IN TREATING DISORDERS OF THE CENTRAL NERVOUS SYSTEM

RELATED APPLICATION

Figure 1A:
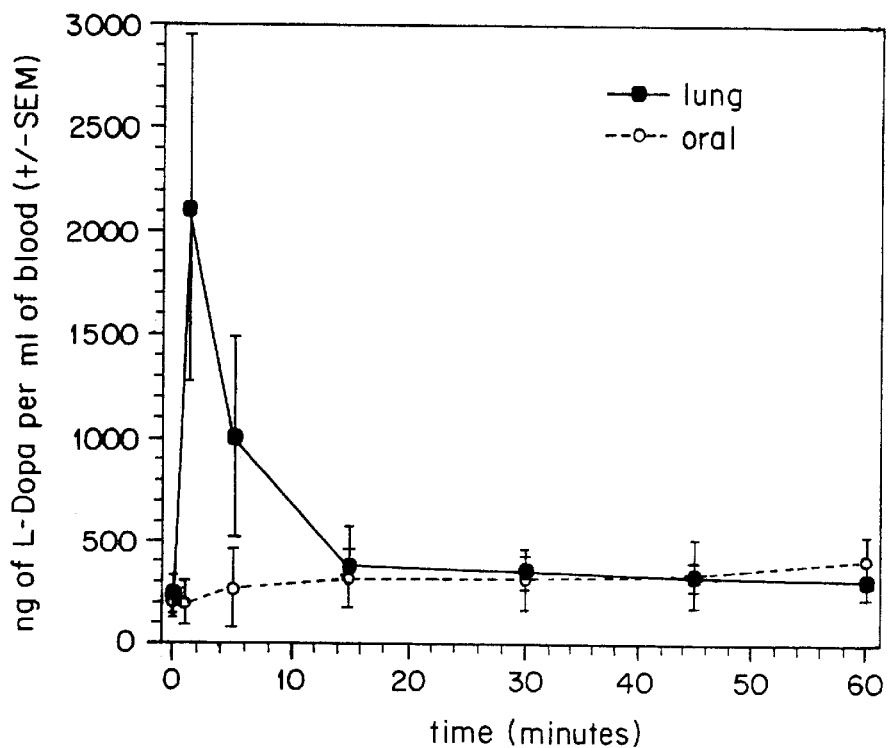

This application is a Continuation-in-Part of U.S. patent application Ser. No. 09/665,252, filed on Sep. 19, 2000, U.S. Pat. No. 6,514,482, the entire contents of which are incorporated herein by reference.

BACKGROUND OF THE INVENTION

Parkinson's disease is characterized neuropathologically by degeneration of dopamine neurons in the basal ganglia and neurologically by debilitating tremors, slowness of movement and balance problems. It is estimated that over one million people suffer from Parkinson's disease. Nearly all patients receive the dopamine precursor levodopa or L-Dopa, often in conjunction with the dopa-decarboxylase inhibitor, carbidopa. L-Dopa adequately controls symptoms of Parkinson's disease in the early stages of the disease. However, it tends to become less effective after a period which can vary from several months to several years in the course of the disease.

It is believed that the varying effects of L-Dopa in Parkinson's disease patients is related, at least in part, to the plasma half life of L-Dopa which tends to be very short, in the range of 1 to 3 hours, even when co-administered with carbidopa. In the early stages of the disease, this factor is mitigated by the dopamine storage capacity of the targeted striatal neurons. L-Dopa is taken up and stored by the neurons and is released over time. However, as the disease progresses, dopaminergic neurons degenerate, resulting in decreased dopamine storage capacity. Accordingly, the positive effects of L-Dopa become increasingly related to fluctuations of plasma levels of L-Dopa. In addition, patients tend to develop problems involving gastric emptying and poor intestinal uptake of L-Dopa. Patients exhibit increasingly marked swings in Parkinson's disease symptoms, ranging from a return to classic Parkinson's disease symptoms, when plasma levels fall, to the so-called dyskinesis, when plasma levels temporarily rise too high following L-Dopa administration.

As the disease progresses, conventional L-Dopa therapy involves increasingly frequent, but lower dosing schedules. Many patients, for example, receive L-Dopa every two to three hours. It is found, however, that even frequent doses of L-Dopa are inadequate in controlling Parkinson's disease symptoms. In addition, they inconvenience the patient and often result in non-compliance.

It is also found that even with as many as six to ten L-Dopa doses a day, plasma L-Dopa levels can still fall dangerously low, and the patient can experience very severe Parkinson's disease symptoms. When this happens, additional L-Dopa is administered as intervention therapy to rapidly increase brain dopamine activity. However, orally administered therapy is associated with an onset period of about 30 to 45 minutes during which the patient suffers unnecessarily. In addition, the combined effects of the intervention therapy, with the regularly scheduled dose can lead to overdosing, which can require hospitalization. For example, subcutaneously administered dopamine receptor agonist (apomorphine), often requiring a peripherally acting dopamine antagonist, for example, domperidone, to control dopamine-induced nausea, is inconvenient and invasive.

Other medical indications involving the central nervous system (CNS) require rapid delivery of a medicament such as but not limited to epilepsy, panic attacks and migraines. For example, about 2 million people in the USA suffer from some form of epilepsy, with the majority receiving at least one of several different anti-seizure medications. The incidence of status epilepticus (the more serious form of epilepsy) is approximately 250,000. A significant number of patients also suffer from so-called "cluster seizures", wherein an initial seizure forewarns that a series of additional seizures will occur within a relatively short time frame. By some reports, 75% of all patients continue to experience seizures despite taking medication chronically. Poor compliance with the prescribed medications is believed to be a significant (albeit not sole) contributing factor. The importance of controlling or minimizing the frequency and intensity of seizures lies in the fact that incidence of seizures has been correlated with neuronal deficits and is believed to cause loss of neurons in the brain.

Despite chronic treatment, as many as 75% of all patients continue to exhibit periodic seizures. The uncontrolled seizures occur in many forms. In the case of "cluster seizures," one seizure serves notice that a cascade has begun which will lead to a series of seizures before the total episode passes. In certain patients, prior to the onset of a severe seizure, some subjective feeling or sign is detected by the patient (defined as an aura). In both instances, an opportunity exists for these patients to significantly reduce the liability of the seizure through "self medication". While many patients are instructed to do so, the drugs currently available to permit effective self medication are limited.

Panic attacks purportedly affect at least about 2.5 million people in this country alone. The disorder is characterized by acute episodes of anxiety, leading to difficult breathing, dizziness, heart palpitations and fear of losing control. The disorder is believed to involve a problem with the sympathetic nervous system (involving an exaggerated arousal response, leading to overstimulation of adrenaline release and/or adrenergic neurons). Current pharmacotherapy combines selective serotonin re-uptake inhibitors (SSRIs), or other antidepressant medications, with the concomitant use of benzodiazapines.

A limitation of the pharmacotherapies in current use is the delay in the onset of efficacy at the beginning of treatment. Like treatments for depression, the onset of action of the SSRIs requires weeks rather than days. The resulting requirement for continuous prophylactic treatment can, in turn, lead to significant compliance problems rendering the treatment less effective. Therefore, there is a need for rapid onset therapy at the beginning of treatment to manage the anticipation of the panic attacks, as well as a treatment for aborting any attacks as soon as possible after their occurrence.

A pure vasogenic etiology/pathogenesis for migraine was first proposed in the 1930s; by the 1980s, this was replaced by a neurogenic etiology/pathogenesis, which temporarily won favor among migraine investigators. However, it is now generally recognized that both vasogenic and neurogenic components are involved, interacting as a positive feedback system, with each continuously triggering the other. The major neurotransmitters implicated include serotonin (the site of action of the triptans), substance P (traditionally associated with mediating pain), histamine (traditionally associated with inflammation) and dopamine. The major pathology associated with migraine attacks include an inflammation of the dura, an increase in diameter of meningeal vessels and supersensitivity of the trigeminal cranial nerve, including the branches that enervate the meningeal vessels. The triptans are believed to be effective because they affect both the neural and vascular components of the migraine pathogenic cascade. Migraines include Classic and Common Migraines, Cluster Headaches and Tension Headaches.

Initial studies with sumatriptain showed that, when administered intravenously (IV), a 90% efficacy rate was achieved. However, the efficiency rate is only approximately 60% with the oral form (versus 30% for placebo). The nasal form has proven to be highly variable, requiring training and skill on the part of the patient, which some of the patients do not seem to master. The treatment also induces a bad taste in the mouth which many patients find highly objectionable. There currently exists no clear evidence that any of the recent, more selective 5HT1 receptor agonists are any more efficacious than sumatriptan (which stimulates multiple receptor subtypes; e.g., 1B, 1D, and 1F).

In addition to not providing adequate efficacy, current dosing of triptans have at least two other deficiencies: (1) vasoconstriction of chest and heart muscles, which produces chest tightness and pain in some subjects; this effect also presents an unacceptable risk to hypertensive and other CV patients, for whom the triptans are contraindicated, and (2) the duration of action of current formulations is limited, causing a return of headache in many patients about 4 hours after initial treatment.

Rapid onset of a hypnotic would also be quite desirable and particularly useful in sleep restoration therapy, as middle of night awakening and difficulty in falling asleep again, once awakened, is common in middle aged and aging adults.

Other indications related to the CNS, such as, for example, mania, bipolar disorders, schizophrenia, appetite suppression, motion sickness, nausea and others, as known in the art, also require rapid delivery of a medicament to its site of action.

Therefore, a need exists for methods of delivery of medicaments which are at least as effective as conventional therapies yet minimize or eliminate the above-mentioned problems.

SUMMARY OF THE INVENTION

The invention relates to methods of treating disorders of the central nervous system (CNS). More specifically the invention relates to methods of delivering a drug suitable in treating a disorder of the CNS to the pulmonary system and include administering to the respiratory tract of a patient in need of treatment particles comprising an effective amount of the medicament. In one embodiment, the patient is in need of rapid onset of the treatment, for instance in need of rescue therapy; the medicament is released into the patient's blood stream and reaches the medicament's site of action in a time interval which is sufficiently short to provide the rescue therapy or rapid treatment onset. In another embodiment, the invention is related to providing ongoing, non-rescue therapy to a patient suffering with a disorder of the CNS.

Disorders of the nervous system include, for example, Parkinson's disease, epileptic and other seizures, panic attacks, sleep disorders, migraines, attention deficit hyperactivity disorders, Alzheimer's disease, bipolar disorders, obsessive compulsive disorders and others.

The methods of the invention are particularly useful in the ongoing treatment and for rescue therapy in the course of Parkinson's disease. The drug or medicament employed in the methods of the invention is a dopamine precursor or a dopamine agonist, for example, levodopa (L-DOPA).

In one embodiment, the invention is related to a method for treating Parkinson's disease includes administering to the respiratory tract of a patient in need of treatment or rescue therapy a drug for treating Parkinson's disease, e.g., L-Dopa. The drug is delivered to the pulmonary system, for instance to the alveoli region of the lung. In comparison to oral administration, at least about a two fold dose reduction is employed. Doses generally are between about two times and about ten times less than the dose required with oral administration.

In other embodiments, a method for treating a disorder of the CNS includes administering to the respiratory tract of a patient in need of treatment a drug for treating the disorder. The drug is administered in a dose which is at least about two times less than the dose required with oral administration and is delivered to the pulmonary system.

The doses employed in the invention generally also are at least about two times less than the dose required with routes of administration other than intravenous, such as, for instance, subcutaneous injection, intramuscular injection, intra-peritoneal, buccal, rectal and nasal.

The invention further is related to methods for administering to the pulmonary system a therapeutic dose of the medicament in a small number of steps, and preferably in a single, breath activated step. The invention also is related to methods of delivering a therapeutic dose of a drug to the pulmonary system, in a small number of breaths, and preferably in a single breath. The methods include administering particles from a receptacle which has a mass of particles, to a subject's respiratory tract. Preferably, the receptacle has a volume of at least about 0.37 $cm^3$ and can have a design suitable for use in a dry powder inhaler. Larger receptacles having a volume of at least about 0.48 $cm^3$, 0.67 $cm^3$ or 0.95 $cm^3$ also can be employed. The receptacle can be held in a single dose breath activated dry powder inhaler.

In one embodiment of the invention, the particles deliver at least about 10 milligrams (mg) of the drug. In other embodiments, the particles deliver at least about 15, 20, 25, 30 milligrams of drug. Higher amounts can also be delivered, for example the particles can deliver at least about 35, 40 or 50 milligrams of drug.

The invention also is related to methods for the efficient delivery of particles to the pulmonary system. In one embodiment, the invention is related to delivering to the pulmonary system particles that represent at least about 70% and preferably at least about 80% of the nominal powder dose. In another embodiment of the invention, a method of delivering a medicament to the pulmonary system, in a single, breath-activated step, includes administering particles, from a receptacle which has a mass of particles, to the respiratory tract of a subject, wherein at least 50% of the mass of particles is delivered.

Preferably, administration to the respiratory tract is by a dry powder inhaler or by a metered dose inhaler. The particles of the invention also can be employed in compositions suitable for delivery to the pulmonary system such as known in the art.

In one embodiment, particles employed in the method of the invention are particles suitable for delivering a medicament to the pulmonary system and in particular to the alveoli or the deep lung. In a preferred embodiment, the particles have a tap density which is less than 0.4 $g/cm^3$. In another preferred embodiment, the particles have a geometric diameter, of at least 5 $\mu m$ (microns), preferably between about 5 $\mu m$ and 30 $\mu m$. In yet another preferred embodiment, the particles have an aerodynamic diameter between about 1 $\mu m$ and about 5 $\mu m$. In another embodiment, the particles have a mass median geometric diameter (MMGD) larger than 5 μm, preferably around about 10 μm or larger. In yet another embodiment, the particles have a mass median aerodynamic diameter (MMAD) ranging from about 1 μm to about 5 μm. In a preferred embodiment, the particles have an MMAD ranging from about 1 μm tobout 3 μm.

Particles can consist of the medicament or can further include one or more additional components. Rapid release of the medicament into the blood stream and its delivery to its site of action, for example, the central nervous system, is preferred. In one embodiment of the invention, the particles include a material which enhances the release kinetics of the medicament. Examples of suitable such materials include, but are not limited to, certain phospholipids, amino acids, carboxylate moieties combined with salts of multivalent metals and others.

In a preferred embodiment, the energy holding the particles of the dry powder in an aggregated state is such that a patient's breath, over a reasonable physiological range of inhalation flow rates is sufficient to deaggregate the powder contained in the receptacle into respirable particles. The deaggregated particles can penetrate via the patient's breath into and deposit in the airways and/or deep lung with high efficiency.

The invention has many advantages. For example, pulmonary delivery provides on-demand treatment without the inconvenience of injections. Selective delivery of a medicament to the central nervous system can be obtained in a time frame not available with other administration routes, in particular conventional oral regimens. Thus, an effective dose can be delivered to the site of action on the "first pass" of the medicament in the circulatory system. By practicing the invention, relief is available to symptomatic patients in a time frame during which conventional oral therapies would still be traveling to the site of action. The reduced doses employed in the methods of the invention result in a plasma drug level which is equivalent to that obtained with the oral dose. Blood plasma levels approaching those observed with intravenous administration can be obtained. Dose advantages over other routes of administration, e.g., intramuscular, subcutaneous, intra-peritoneal, buccal, rectal and nasal, also can be obtained. Furthermore, a therapeutic amount of the drug can be delivered to the pulmonary system in one or a small number of steps or breaths.

BRIEF DESCRIPTION OF THE DRAWINGS

FIG. 1A is a plot representation of blood levels of L-Dopa in rats following administration via oral gavage or direct administration to the lungs measured by mass spectrometer.

FIG. 1B is a plot representation of blood levels of L-Dopa in rats following administration via oral gavage or direct administration to the lungs measured by HPLC.

FIG. 2A is a plot representation of blood L-Dopa levels in rats following delivery orally or directly into the lungs.

FIG. 2B is a plot representation of striatal dopamine levels in rats following delivery of L-Dopa orally or directly into the lungs.

FIG. 3 is a plot representation of blood and striatal levels of $^{14}C$ following administration of $^{14}C$-L-Dopa either orally or directly to the lungs.

FIG. 4 is a plot representation of plasma $^{14}C$ levels in rats following $^{14}C$-L-Dopa administration via oral (gavage), tracheotomy or ventilator.

FIG. 5 is a plot representation of brain $^{14}C$ levels in rats following $^{14}C$-L-Dopa administration via oral (gavage), tracheotomy or ventilator.

FIG. 6A is a bar graph showing absolute $^{14}C$-Carboplatin levels in regions of the brain following intravenous (IV) and pulmonary (lung) administration.

FIG. 6B is a bar graph showing relative $^{14}C$-Carboplatin levels in regions of the brain following intravenous (IV) and pulmonary (lung) administration.

FIG. 7A is a bar graph showing absolute $^{14}C$-Carboplatin levels in animal organs following intravenous (IV) or pulmonary (lung) administration.

FIG. 7B shows relative $^{14}C$-Carboplatin levels in animal organs following intravenous (IV) or pulmonary (lung) administration.

FIG. 8 is a plot representation showing plasma concentration of L-Dopa vs. time following oral or pulmonary administration (normalized for an 8 mg dose).

FIG. 9 is a plot representation showing plasma concentration of ketoprofen vs. time for oral and pulmonary groups.

FIG. 10 is a plot representation showing plasma concentration of ketoprofen vs. time for oral group FIG. 11 is a plasma concentration of ketoprofen vs. time for pulmonary group.

FIG. 12 is a plot showing RODOS curves for different powder formulations that include L-DOPA.

FIGS. 13A and 13B are HPLC chromatograms that depict L-DOPA recovery from powders (FIG. 13A) compared to a blank sample (FIG. 13B).

FIG. 14A depicts L-DOPA plasma levels following pulmonary (lung), and oral routes.

FIG. 14B depicts L-DOPA plasma levels following pulmonary (lung), oral and intravenous administration.

FIGS. 15A and 15B show results, respectively, of oral (p.o.) and pulmonary (lung) L-DOPA on functional "placing task" in a rat model of Parkinson's disease.

FIGS. 16A and 16B show results, respectively of oral (p.o.) and pulmonary (lung) L-DOPA on functional "bracing task" in a rat model of Parkinson's disease.

FIGS. 17A and 17B show results, respectively of oral (p.o.) and pulmonary (lung) L-DOPA on functional akinesia task in a rat model of Parkinson's disease.

FIG. 18 shows results of oral (p.o.) and pulmonary (lung) delivery of L-DOPA on functional rotation in a rat model of Parkinson's disease.

FIG. 19A depicts time to seizure onset after delivery of pulmonary and oral alprazolam 10 minutes prior to PZT administration.

FIG. 19B depicts duration of seizure after delivery of pulmonary and oral alprazolam 10 minutes prior to PZT administration.

FIG. 20A depicts time to seizure onset after delivery of pulmonary and oral alprazolam 30 minutes prior to PZT administration.

FIG. 20B depicts duration of seizure after delivery of pulmonary and oral alprazolam 30 minutes prior to PZT administration.

FIG. 21A depicts time to seizure onset for pulmonary alprazolam 10 and 30 minutes prior to PZT administration.

FIG. 21B depicts duration of seizure for pulmonary alprazolam 10 and 30 minutes prior to PZT administration.

DETAILED DESCRIPTION OF THE INVENTION

The features and other details of the invention, either as steps of the invention or as combination of parts of the invention, will now be more particularly described and pointed out in the claims. It will be understood that the particular embodiments of the invention are shown by way of illustration and not as limitations of the invention. The principle feature of this invention may be employed in various embodiments without departing from the scope of the invention.

The invention is generally related to methods of treating disorders of the CNS. In particular, the invention is related to methods for pulmonary delivery of a drug, medicament or bioactive agent.

One preferred medical indication which can be treated by the method of the invention is Parkinson's disease, in particular during the late stages of the disease, when the methods described herein particularly well suited to provide rescue therapy. As used herein, "rescue therapy" means on demand, rapid delivery of a drug to a patient to help reduce or control disease symptoms. The methods of the invention also are suitable for use in patients in acute distress observed in disorders of the CNS. In other embodiments, the methods and particles disclosed herein can be used in the ongoing (non-rescue) treatment of Parkinson's disease.

In addition to Parkinson's disease, forms of epileptical seizures such as occurring in Myoclonic Epilepsies, including Progressive and Juvenile; Partial Epilepsies, including Complex Partial, Frontal Lobe, Motor and Sensory, Rolandic and Temporal Lobe; Benign Neonatal Epilepsy; Post-Traumatic Epilepsy; Reflex Epilepsy; Landau-Kleffner Syndrome; and Seizures, including Febrile, Status Epilepticus, and Epilepsia Partialis Continua also can be treated using the method of the invention.

Attention deficit/hyperactivity disorders (ADHD) also can be treated using the methods and formulations of the invention.

Sleep disorders that can benefit from the present invention include Dyssomnias, Sleep Deprivation, Circadian Rhythm Sleep Disorders, Intrinsic Sleep Disorders, including Disorders of Excessive Somnolence, Idiopathic Hypersomnolence, Kleine-Levin Syndrome, Narcolepsy, Nocturnal Myoclonus Syndrome, Restless Legs Syndrome, Sleep Apnea Syndromes, Sleep Initiation and Maintenance Disorders, Parasomnias, Nocturnal Nyoclonus Syndrome, Nocturnal Paroxysmal Dystonia, REM Sleep Parasomnias, Sleep Arousal Disorders, Sleep Bruxism, and Sleep-Wake Transition Disorders. Sleep interruption often occurs around 2 to 3 a.m. and requires treatment the effect of which lasts approximately 3 to 4 hours.

Examples of other disorders of the central nervous system which can be treated by the method of the invention include but are not limited to appetite suppression, motion sickness, panic or anxiety attack disorders, nausea suppressions, mania, bipolar disorders, schizophrenia and others, known in the art to require rescue therapy.

Medicaments which can be delivered by the method of the invention include pharmaceutical preparations such as those generally prescribed in the rescue therapy of disorders of the nervous system. In a preferred embodiment, the medicament is a dopamine precursor, dopamine agonist or any combination thereof. Preferred dopamine precursors include levodopa (L-Dopa). Other drugs generally administered in the treatment of Parkinson's disease and which may be suitable in the methods of the invention include, for example, ethosuximide, dopamine agonists such as, but not limited to carbidopa, apomorphine, sopinirole, pramipexole, pergoline, bronaocriptine. The L-Dopa or other dopamine precursor or agonist may be any form or derivative that is biologically active in the patient being treated.

Examples of anticonvulsants include but are not limited to diazepam, valproic acid, divalproate sodium, phenytoin, phenytoin sodium, cloanazepam, primidone, phenobarbital, phenobarbital sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione. Other anticonvulsant drugs include, for example, acetazolamide, carbamazepine, chlormethiazole, clonazepam, clorazepate dipotassium, diazepam, dimethadione, estazolam, ethosuximide, flunarizine, lorazepam, magnesium sulfate, medazepam, melatonin, mephenytoin, mephobarbital, meprobamate, nitrazepam, paraldehyde, phenobarbital, phenytoin, primidone, propofol, riluzole, thiopental, tiletamine, trimethadione, valproic acid, vigabatrin. Benzodiazepines are preferred drugs. Examples include, but are not limited to, alprazolam, chlordiazepoxide, clorazepate dipotassium, estazolam, medazepam, midazolam, triazolam, as well as benzodiazepinones, including anthramycin, bromazepam, clonazepam, devazepide, diazepam, flumazenil, flunitrazepam, flurazepam, lorazepam, nitrazepam, oxazepam, pirensepine, prazepam, and temazepam.

Examples of drugs for providing symptomatic relief for migraines include the non-steroidal anti-inflammatory drugs (NSAIDs). Generally, parenteral NSAIDs are more effective against migraine than oral forms. Among the various NSAIDs, ketoprofen is considered by many to be one of the more effective for migraine. Its $T_{max}$ via the oral route, however, is about 90 min. Other NSAIDs include aminopyrine, amodiaquine, ampyrone, antipyrine, apazone, aspirin, benzydamine, bromelains, bufexamac, BW-755C, clofazimine, clonixin, curcumin, dapsone, diclofenac, diflunisal, dipyrone, epirizole, etodolac, fenoprofen, flufenamic acid, flurbiprofen, glycyrrhizic acid, ibuprofen, indomethacin, ketorolac, ketorolac tromethamine, meclofenamic acid, mefenamic acid, mesalamine, naproxen, niflumic acid, oxyphenbutazone, pentosan sulfuric polyester, phenylbutazone, piroxicam, prenazone, salicylates, sodium salicylate, sulfasalazine, sulindac, suprofen, and tolmetin.

Other antimigraine agents include triptans, ergotamine tartrate, propanolol hydrochloride, isometheptene mucate, dichloralphenazone, and others.

Agents administered in the treatment of ADHD include, among others, methylpenidate, dextroamphetamine, pemoline, imipramine, desipramine, thioridazine and carbamazepine.

Preferred drugs for sleep disorders include the benzodiazepines, for instance, alprazolam, chlordiazepoxide, clorazepate dipotassium, estazolam, medazepam, midazolam, triazolam, as well as benzodiazepinones, including anthramycin, bromazepam, clonazepam, devazepide, diazepam, flumazenil, flunitrazepam, flurazepam, lorasepam, nitrazepam, oxazepam, pirenzepine, prazepam, temazepam, and triazolam. Another drug is zolpidem (Ambien®, Lorex) which is currently given as a 5 mg tablet with $T_{max}$=1.6 hours; ½ Life=2.6 hours (range between 1.4 to 4.5 hours). Peak plasma levels are reached in about 2 hours with a half-life of about 1.5 to 5.5 hours. Still another drug is triazolam (Halcion®, Pharmacia) which is a heterocyclic benzodiazepine derivative with a molecular weight of 343 which is soluble in alcohol but poorly soluble in water. The usual dose by mouth is 0.125 and 0.25 mg. Temazepam may be a good candidate for sleep disorders due to a longer duration of action that is sufficient to maintain sleep throughout the night. Zaleplon (Sonata®, Wyeth Ayerst) is one drug currently approved for middle of night sleep restoration due to its short duration of action.

Other medicaments include analgesics/antipyretics for example, ketoprofen, flurbiprofen, aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and others.

Antianxiety medicaments include, for example, lorazepam, buspirone hydrochloride, prazepam, chlordizepoxide hydrochloride, oxazepam, clorazepate dipotassium, diazepam, hydroxyzine pamoate, hydroxyzine hydrochloride, alprazolam, droperidol, halazepam, chlormezanone, and others.

Examples of antipsychotic agents include haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like.

One example of an antimonic agent is lithium carbonate while examples of Alzheimer agents include tetra amino acridine, donapezel, and others.

Sedatives/hypnotics include barbiturates (e.g., pentobarbital, phenobarbital sodium, secobarbital sodium), benzodiazepines (e.g., flurazepam hydrochloride, triazolam, tomazeparm, midazolam hydrochloride), and others.

Hypoglycemic agents include, for example, ondansetron, granisetron, meclizine hydrochloride, nabilone, prochlorperazine, dimenhydrinate, promethazine hydrochloride, thiethylperazine, scopolamine, and others. Antimotion sickness agents include, for example, cinnorizine.

Combinations of drugs also can be employed.

In one embodiment of the invention the particles consist of a medicament, such as, for example, one of the medicaments described above. In another embodiment, the particles include one or more additional components. The amount of drug or medicament present in these particles can range 1.0 to about 90.0 weight percent.

For rescue therapy, particles that include one or more component(s) which promote(s) the fast release of the medicament into the blood stream are preferred. As used herein, rapid release of the medicament into the blood stream refers to release kinetics that are suitable for providing rescue therapy. In one embodiment, optimal therapeutic plasma concentration is achieved in less than 10 minutes. It can be achieved in as fast as about 2 minutes and even less. Optimal therapeutic concentration often can be achieved in a time frame similar or approaching that observed with intravenous administration. Generally, optimal therapeutic plasma concentration is achieved significantly faster than that possible with oral administration, for example, 2 to 10 times faster.

In a preferred embodiment, the particles include one or more phospholipids, such as, for example, a phosphatidylcholine, phosphatidylethanolamine, phosphatidylglycerol, phosphatidylserine, phosphatidylinositol or a combination thereof. In one embodiment, the phospholipids are endogenous to the lung. Combinations of phospholipids can also be employed. Specific examples of phospholipids are shown in Table 1.

TABLE 1

| | |
|---|---|
| Dilaurylolyphosphatidylcholine (C12;0) | DLPC |
| Dimyristoylphosphatidylcholine (C14;0) | DMPC |
| Dipalmitoylphosphatidylcholine (C16:0) | DPPC |
| Distearoylphosphatidylcholine (18:0) | DSPC |
| Dioleoylphosphatidylcholine (C18:1) | DOPC |
| Dilaurylolyphosphatidylglycerol | DLPG |
| Dimyristoylphosphatidylglycerol | DMPG |
| Dipalmitoylphosphatidylglycerol | DPPG |
| Distearoylphosphatidylglycerol | DSPG |
| Dioleoylphosphatidylglycerol | DOPG |
| Dimyristoyl phosphatidic acid | DMPA |
| Dimyristoyl phosphatidic acid | DMPA |
| Dipalmitoyl phosphatidic acid | DPPA |
| Dipalmitoyl phosphatidic acid | DPPA |
| Dimyristoyl phosphatidylethanolamine | DMPE |
| Dipalmitoyl phosphatidylethanolamine | DPPE |
| Dimyristoyl phosphatidylserine | DMPS |
| Dipalmitoyl phosphatidylserine | DPPS |
| Dipalmitoyl sphingomyelin | DPSP |
| Distearoyl sphingomyelin | DSSP |

The phospholipid can be present in the particles in an amount ranging from about 0 to about 90 weight %. Preferably, it can be present in the particles in an amount ranging from about 10 to about 60 weight %.

The phospholipids or combinations thereof can be selected to impart control release properties to the particles. Particles having controlled release properties and methods of modulating release of a biologically active agent are described in U.S. Provisional Patent Application No. 60/150,742 entitled Modulation of Release From Dry Powder Formulations by Controlling Matrix Transition, filed on Aug. 25, 1999, U.S. Non-Provisional patent application Ser. No. 09/644,736, filed on Aug. 23, 2000, with the title Modulation of Release From Dry Powder Formulations and U.S. Non-Provisional patent application Ser. No. 09/792,869 filed on Feb. 23, 2001, under Attorney Docket No. 2685.1012-004, and with the title Modulation of Release From Dry Powder Formulations. The contents of all three applications are incorporated herein by reference in their entirety. Rapid release, preferred in the delivery of a rescue therapy medicament, can be obtained for example, by including in the particles phospholipids characterized by low transition temperatures. In another embodiment, a combination of rapid with controlled release particles would allow a rescue therapy coupled with a more sustained release in a single cause of therapy. Control release properties can be utilized in non-rescue, ongoing treatment of a disorder of the CNS.

In another embodiment of the invention the particles can include a surfactant. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

In addition to lung surfactants, such as, for example, phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); and tyloxapol.

The surfactant can be present in the particles in an amount ranging from about 0 to about 90 weight %. Preferably, it can be present in the particles in an amount ranging from about 10 to about 60 weight %.

Methods of preparing and administering particles including surfactants, and, in particular phospholipids, are disclosed in U.S. Pat. No 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety.

In another embodiment of the invention, the particles include an amino acid. Hydrophobic amino acids are preferred. Suitable amino acids include naturally occurring and non-naturally occurring hydrophobic amino acids. Examples of amino acids which can be employed include, but are not limited to: glycine, proline, alanine, cysteine, methionine, valine, leucine, tyrosine, isoleucine, phenylalanine, tryptophan. Preferred hydrophobic amino acids, include but are not limited to, leucine, isoleucine, alanine, valine, phenylalanine, glycine and tryptophan. Amino acids include combinations of hydrophobic amino acids can also be employed. Non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1–C8 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), —CONH$_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophillic.

A number of the suitable amino acids, amino acids analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Combinations of hydrophobic amino acids can also be employed. Furthermore, combinations of hydrophobic and hydrophilic (preferentially partitioning in water) amino acids, where the overall combination is hydrophobic, can also be employed. Combinations of one or more amino acids and one or more phospholipids or surfactants can also be employed. Materials which impart fast release kinetics to the medicament are preferred.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10% weight. Preferably, the amino acid salt is present in the particles in an amount ranging from about 20 to about 80 weight %. Methods of forming and delivering particles which include an amino acid are described in U.S. patent application Ser. No. 09/382,959, filed on Aug. 25, 1999, entitled Use of Simple Amino Acids to Form Porous Particles During Spray Drying and in U.S. Non-Provisional Patent Application No. 09/644,320, filed on Aug. 23, 2000, titled Use of Simple Amino Acids to Form Porous Particles, the teachings of both are incorporated herein by reference in their entirety.

In another embodiment of the invention, the particles include a carboxylate moiety and a multivalent metal salt. One or more phospholipids also can be included. Such compositions are described in U.S. Provisional Application No. 60/150,662, filed on Aug. 25, 1999, entitled Formulation for Spray-Drying Large Porous Particles, and U.S. Non-Provisional Patent Application No. 09/644,105, filed on Aug. 23, 2000, titled Formulation for Spray-Drying Large Porous Particles, the teachings of both are incorporated herein by reference in their entirety. In a preferred embodiment, the particles include sodium citrate and calcium chloride.

Other materials, preferably materials which promote fast release kinetics of the medicament can also be employed. For example, biocompatible, and preferably biodegradable polymers can be employed. Particles including such polymeric materials are described in U.S. Pat. No. 5,874,064, issued on Feb. 23, 1999 to Edwards et al., the teachings of which are incorporated herein by reference in their entirety.

The particles can also include a material such as, for example, dextran, polysaccharides, lactose, trehalose, cyclodextrins, proteins, peptides, polypeptides, fatty acids, inorganic compounds, phosphates.

In one specific example, the particles include (by weight percent) 50% L-Dopa, 25% DPPC, 15% sodium citrate and 10% calcium chloride. In another specific example, the particles include (by weight percent) 50% L-Dopa, 40% leucine and 10% sucrose. In yet another embodiment the particles include (by weight percent) 10% benzodiazepine, 20% sodium citrate, 10% calcium chloride and 60% DPPC.

In a preferred embodiment, the particles of the invention have a tap density less than about 0.4 g/cm$^3$. Particles which have a tap density of less than about 0.4 g/cm$^3$ are referred herein as "aerodynamically light particles". More preferred are particles having a tap density less than about 0.1 g/cm$^3$. Tap density can be measured by using instruments known to those skilled in the art such as but not limited to the Dual Platform Microprocessor Controlled Tap Density Tester (Vankel, N.C.) or a GeoPyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopeia convention, Rockville, Md, 10$^{th}$ Supplement, 4950–4951, 1999. Features which can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

Aerodynamically light particles have a preferred size, e.g., a volume median geometric diameter (VMGD) of at least about 5 microns ($\mu$m). In one embodiment, the VMGD is from about 5 $\mu$m to about 30 $\mu$m. In another embodiment of the invention, the particles have a VMGD ranging from about 10 $\mu$m to about 30 $\mu$m. In other embodiments, the particles have a median diameter, mass median diameter (MMD), a mass median envelope diameter (MMED) or a mass median geometric diameter (MMGD) of at least 5 $\mu$m, for example from about 5 $\mu$m and about 30 $\mu$m.

The diameter of the spray-dried particles, for example, the VMGD, can be measured using an electrical zone sensing instrument such as a Multisizer IIe, (Coulter Electronic, Luton, Beds, England), or a laser diffraction instrument (for example Helos, manufactured by Sympatec, Princeton, N.J.). Other instruments for measuring particle diameter are well know in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter", between about 1 $\mu$m and about 5 $\mu$m. In another embodiment of the invention, the MMAD is between about 1 $\mu$m and about 3 $\mu$m. In a further embodiment, the MMAD is between about 3 $\mu$m and about 5 $\mu$m.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

The aerodynamic diameter, $d_{aer}$, can be calculated from the equation:

$$d_{aer}=d_g\sqrt{\rho_{tap}}$$

where $d_g$ is the geometric diameter, for example the MMGD, and $\rho$ is the powder density.

Particles which have a tap density less than about 0.4 g/cm$^3$, median diameters of at least about 5 $\mu$m, and an aerodynamic diameter of between about 1 $\mu$m and about 5 $\mu$m, preferably between about 1 $\mu$m and about 3 $\mu$m, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 $\mu$m, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 $\mu$m. Kawaguchi, H., et al., *Biomaterials* 7: 61–66 (1986); Krenis, L. J. and Strauss, B., *Proc. Soc. Exp. Med.*, 107: 748–750 (1961); and Rudt, S. and Muller, R. H., *J. Contr. Rel.*, 22: 263–272 (1992). For particles of statistically isotropic shape, such as spheres with rough surfaces, the particle envelope volume is approximately equivalent to the volume of cytosolic space required within a macrophage for complete particle phagocytosis.

The particles maybe fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 $\mu$m are preferred for delivery to the central and upper airways. Particles having and aerodynamic diameter ranging from about 1 to about 3 $\mu$m are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 $\mu$m), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp.95–117, Stuttgart: Medpharm Scientific Publishers, 1992)), by the formula:

$$d_{aer}=d\sqrt{\rho}$$

where the envelope mass ρ is in units of g/cm³. Maximal deposition of monodispersed aerosol particles in the alveolar region of the human lung (~60%) occurs for an aerodynamic diameter of approximately $d_{aer}$=3 μm. Heyder, J. et al., *J. Aerosol Sci.*, 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho} \; \mu m \; (\text{where } \rho<1 \text{ g/cm}^3);$$

where d is always greater than 3 μm. For example, aerodynamically light particles that display an envelope mass density, ρ=0.1 g/cm³, will exhibit a maximum deposition for particles having envelope diameters as large as 9.5 μm. The increased particle size diminishes interparticle adhesion forces. Visser, J., *Powder Technology,* 58: 1–10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

In another embodiment of the invention, the particles have an envelope mass density, also referred to herein as "mass density" of less than about 0.4 g/cm³. Particles also having a mean diameter of between about 5 μm and about 30 μm are preferred. Mass density and the relationship between mass density, mean diameter and aerodynamic diameter are discussed in U.S. application Ser. No. 08/655,570, filed on May 24, 1996, which is incorporated herein by reference in its entirety. In a preferred embodiment, the aerodynamic diameter of particles having a mass density less than about 0.4 g/cm³ and a mean diameter of between about 5 μm and about 30 μm mass mean aerodynamic diameter is between about 1 μm and about 5 μm.

Suitable particles can be fabricated or separated, for example by filtration or centrifugation, to provide a particle sample with a preselected size distribution. For example, greater than about 30%, 50%, 70%, or 80% of the particles in a sample can have a diameter within a selected range of at least about 5 μm. The selected range within which a certain percentage of the particles must fall may be for example, between about 5 and about 30 μm, or optimally between about 5 and about 15 μm. In one preferred embodiment, at least a portion of the particles have a diameter between about 9 and about 11 μm. Optionally, the particle sample also can be fabricated wherein at least about 90%, or optionally about 95% or about 99%, have a diameter within the selected range. The presence of the higher proportion of the aerodynamically light, larger diameter particles in the particle sample enhances the delivery of therapeutic or diagnostic agents incorporated therein to the deep lung. Large diameter particles generally mean particles having a median geometric diameter of at least about 5 μm.

In a preferred embodiment, suitable particles which can be employed in the method of the invention are fabricated by spray drying. In one embodiment, the method includes forming a mixture including L-Dopa or another medicament, or a combination thereof, and a surfactant, such as, for example, the surfactants described above. In a preferred embodiment, the mixture includes a phospholipid, such as, for example the phospholipids described above. The mixture employed in spray drying can include an organic or aqueous-organic solvent.

Suitable organic solvents that can be employed include but are not limited to alcohols for example, ethanol, methanol, propanol, isopropanol, butanols, and others. Other organic solvents include but are not limited to perfluorocarbons, dichloromethane, chloroform, ether, ethyl acetate, methyl tert-butyl ether and others.

Co-solvents include an aqueous solvent and an organic solvent, such as, but not limited to, the organic solvents as described above. Aqueous solvents include water and buffered solutions. In one embodiment, an ethanol water solvent is preferred with the ethanol:water ratio ranging from about 50:50 to about 90:10 ethanol:water.

The spray drying mixture can have a neutral, acidic or alkaline pH. Optionally, a pH buffer can be added to the solvent or co-solvent or to the formed mixture. Preferably, the pH can range from about 3 to about 10.

Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed. Other spray-drying techniques are well known to those skilled in the art. In a preferred embodiment, a rotary atomizer is employed. An example of suitable spray driers using rotary atomization includes the Mobile Minor spray drier, manufactured by Niro, Denmark. The hot gas can be, for example, air, nitrogen or argon.

In a specific example, 250 milligrams (mg) of L-Dopa in 700 milliliters (ml) of ethanol are combined with 300 ml of water containing 500 mg L-Dopa, 150 mg sodium citrate and 100 mg calcium chloride and the resulting mixture is spray dried. In another example, 700 ml of water containing 500 mg L-Dopa, 100 sucrose and 400 mg leucine are combined with 300 ml of ethanol and the resulting mixture is spray dried.

The particles can be fabricated with a rough surface texture to reduce particle agglomeration and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

The particles of the invention can be employed in compositions suitable for drug delivery to the pulmonary system. For example, such compositions can include the particles and a pharmaceutically acceptable carrier for administration to a patient, preferably for administration via inhalation. The particles may be administered alone or in any appropriate pharmaceutically acceptable carrier, such as a liquid, for example saline, or a powder, for administration to the respiratory system. They can be co-delivered with larger carrier particles, not including a therapeutic agent, the latter possessing mass median diameters for example in the range between about 50 μm and about 100 μm.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6: 273–313, 1990; and in Moren, "Aerosol dosage forms and formulations," in: *Aerosols in Medicine. Principles, Diagnosis and Therapy*, Moren, et al., Eds, Esevier, Amsterdam, 1985.

The method of the invention includes delivering to the pulmonary system an effective amount of a medicament such as, for example, a medicament described above. As used herein, the term "effective amount" means the amount needed to achieve the desired effect or efficacy. The actual effective amounts of drug can vary according to the specific drug or combination thereof being utilized, the particular composition formulated, the mode of administration, and the age, weight, condition of the patient, and severity of the episode being treated. In rescue therapy, the effective amount refers to the amount needed to achieve abatement of symptoms or cessation of the episode. In the case of a dopamine precursor, agonist or combination thereof it is an amount which reduces the Parkinson's symptoms which require rescue therapy. Dosages for a particular patient are described herein and can be determined by one of ordinary skill in the art using conventional considerations, (e.g. by means of an appropriate, conventional pharmacological protocol). For example, effective amounts of oral L-Dopa range from about 50 milligrams (mg) to about 500 mg. In many instances, a common ongoing (oral) L-Dopa treatment schedule is 100 mg eight (8) times a day. During rescue therapy, effective doses of oral L-Dopa generally are similar to those administered in the ongoing treatment.

For being effective during rescue therapy, plasma levels of L-dopa generally are similar to those targeted during ongoing (non-rescue therapy) L-Dopa treatment. Effective amounts of L-Dopa generally result in plasma blood concentrations that range from about 0.5 microgram ($\mu$g)/liter(l) to about 2.0 $\mu$g/l.

It has been discovered in this invention that pulmonary delivery of L-Dopa doses, when normalized for body weight, result in at least a 2-fold increase in plasma level as well as in therapeutical advantages in comparison with oral administration. Significantly higher plasma levels and therapeutic advantages are possible in comparison with oral administration. In one example, pulmonary delivery of L-Dopa results in a plasma level increase ranging from about 2-fold to about 10-fold when compared to oral administration. Plasma levels that approach or are similar to those obtained with intravenous administration can be obtained. Similar findings were made with other drugs suitable in treating disorders of the CNS, such as, for example, ketoprofen.

Assuming that bioavailability remains the same as dosage is increased, the amount of oral drug, e.g. L-Dopa, ketoprofen, required to achieve plasma levels comparable to those resulting from pulmonary delivery by the methods of the invention can be determined at a given point after administration. In a specific example, the plasma levels 2 minutes after oral and administration by the methods of the invention, respectively, are 1 $\mu$g/ml L-Dopa and 5 $\mu$g/ml L-Dopa. Thus 5 times the oral dose would be needed to achieve the 5 $\mu$g/ml level obtained by administering the drug using the methods of the invention. In another example, the L-Dopa plasma levels at 120 minutes after administration are twice as high with the methods of the invention when compared to oral administration. Thus twice as much L-Dopa is required after administration 1 $\mu$g/ml following oral administration in comparison to the amount administered using the methods of the invention.

To obtain a given drug plasma concentration, at a given time after administration, less drug is required when the drug is delivered by the methods of the invention than when it is administered orally. Generally, at least a two-fold dose reduction can be employed in the methods of the invention in comparison to the dose used in conventional oral administration. A much higher dose reduction is possible. In one embodiment of the invention, a five fold reduction in dose is employed and reductions as high as about ten fold can be used in comparison to the oral dose.

At least a two-fold dose reduction also is employed in comparison to other routes of administration, other than intravenous, such as, for example, intramuscular, subcutaneous, buccal, nasal, intra-peritoneal, rectal.

In addition or alternatively to the pharmacokinetic effect, (e.g., serum level, dose advantage) described above, the dose advantage resulting from the pulmonary delivery of a drug, e.g., L-Dopa, used to treat disorders of the CNS, also can be described in terms of a pharmacodynamic response. Compared to the oral route, the methods of the invention avoid inconsistent medicament uptake by intestines, avoidance of delayed uptake following eating, avoidance of first pass catabolism of the drug in the circulation and rapid delivery from lung to brain via aortic artery.

As discussed above, rapid delivery to the medicament's site of action often is desired. Preferably, the effective amount is delivered on the "first pass" of the blood to the site of action. The "first pass" is the first time the blood carries the drug to and within the target organ from the point at which the drug passes from the lung to the vascular system. Generally, the medicament is released in the blood stream and delivered to its site of action within a time period which is sufficiently short to provide rescue therapy to the patient being treated. In many cases, the medicament can reach the central nervous system in less than about 10 minutes, often as quickly as two minutes and even faster.

Preferably, the patient's symptoms abate within minutes and generally no later than one hour. In one embodiment of the invention, the release kinetics of the medicament are substantially similar to the drug's kinetics achieved via the intravenous route. In another embodiment of the invention, the $T_{max}$ of the medicament in the blood stream ranges from about 1 to about 10 minutes. As used herein, the term $T_{max}$ means the point at which levels reach a maximum concentration. In many cases, the onset of treatment obtained by using the methods of the invention is at least two times faster than onset of treatment obtained with oral delivery. Significantly faster treatment onset can be obtained. In one example, treatment onset is from about 2 to about 10 times faster than that observed with oral administration.

If desired, particles which have fast release kinetics, suitable in rescue therapy, can be combined with particles having sustained release, suitable in treating the chronic aspects of a condition. For example, in the case of Parkinson's disease, particles designed to provide rescue therapy can be co-administered with particles having controlled release properties.

The administration of more than one dopamine precursor, agonist or combination thereof, in particular L-Dopa, carbidopa, apomorphine, and other drugs can be provided, either simultaneously or sequentially in time. Carbidopa, for example, is often administered to ensure that peripheral carboxylase activity is completely shut down. Intramuscular, subcutaneous, oral and other administration routes can be employed. In one embodiment, these other agents are delivered to the pulmonary system. These compounds or compositions can be administered before, after or at the same time. In a preferred embodiment, particles that are administered to the respiratory tract include both L-Dopa and carbidopa. The term "co-administration" is used herein to mean that the specific dopamine precursor, agonist or combination thereof and/or other compositions are administered at times to treat the episodes, as well as the underlying conditions described herein.

In one embodiment regular chronic (non-rescue) L-Dopa therapy includes pulmonary delivery of L-Dopa combined with oral carbidopa. In another embodiment, pulmonary delivery of L-Dopa is provided during the episode, while chronic treatment can employ conventional oral administration of L-Dopa/carbidopa.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung or alveoli.

Administration of particles to the respiratory system can be by means such as known in the art. For example, particles are delivered from an inhalation device. In a preferred embodiment, particles are administered via a dry powder inhaler (DPI). Metered-dose-inhalers (MDI), nebulizers or instillation techniques also can be employed.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No. 4,995,385 issued Feb. 26, 1991 to Valentini, et al., and U.S. Pat. No. 5,997,848 issued Dec. 7, 1999 to Patton, et al. Other examples include, but are not limited to, the Spinhaler® (Fisons, Loughborough, U.K.), Rotahaler® (Glaxo-Wellcome, Research Triangle Technology Park, N.C.), FlowCaps® (Hovione, Loures, Portugal), Inhalator® (Boehringer-Ingelheim, Germany), and the Aerolizer® (Novartis, Switzerland), the diskhaler (Glaxo-Wellcome, RTP, N.C.) and others, such as known to those skilled in the art. In one embodiment, the inhaler employed is described in U.S. patent application Ser. No. 09/835,302, entitled Inhalation Device and Method, by David A. Edwards, et al., filed on Apr. 16, 2001. The entire contents of this application are incorporated by reference herein.

The invention further is related to methods for administering to the pulmonary system a therapeutic dose of the medicament in a small number of steps, and preferably in a single, breath activated step. The invention also is related to methods of delivering a therapeutic dose of a drug to the pulmonary system, in a small number of breaths, and preferably in one or two single breaths. The methods includes administering particles from a receptacle having, holding, containing, storing or enclosing a mass of particles, to a subject's respiratory tract.

In one embodiment of the invention, delivery to the pulmonary system of particles is by the methods described in U.S. patent application Ser. No. 09/878,146, High Efficient Delivery of a Large Therapeutic Mass Aerosol, application Ser. No. 09/591,307, filed Jun. 9, 2000, and those described in the Continuation-in-Part of U.S. application Ser. No. 09/591,307, which is filed concurrently herewith. The entire contents of both these applications are incorporated herein by reference. As disclosed therein, particles are held, contained, stored or enclosed in a receptacle. Preferably, the receptacle, e.g. capsule or blister, has a volume of at least about 0.37 $cm^3$ and can have a design suitable for use in a dry powder inhaler. Larger receptacles having a volume of at least about 0.48 $cm^3$, 0.67 $cm^3$ or 0.95 $cm^3$ also can be employed.

In one example, at least 50% of the mass of the particles stored in the inhaler receptacle is delivered to a subject's respiratory system in a single, breath-activated step. In another embodiment, at least 10 milligrams of the medicament is delivered by administering, in a single breath, to a subject's respiratory tract particles enclosed in the receptacle. Amounts as high as 15, 20, 25, 30, 35, 40 and 50 milligrams can be delivered.

In one embodiment, delivery to the pulmonary system of particles in a single, breath-actuated step is enhanced by employing particles which are dispersed at relatively low energies, such as, for example, at energies typically supplied by a subject's inhalation. Such energies are referred to herein as "low." As used herein, "low energy administration" refers to administration wherein the energy applied to disperse and/or inhale the particles is in the range typically supplied by a subject during inhaling.

The invention also is related to methods for efficiently delivering powder particles to the pulmonary system. In one embodiment of the invention, at least about 70% and preferably at least about 80% of the nominal powder dose is actually delivered. As used herein, the term "nominal powder dose" is the total amount of powder held in a receptacle, such as employed in an inhalation device. As used herein, the term nominal drug dose is the total amount of medicament contained in the nominal amount of powder. The nominal powder dose is related to the nominal drug dose by the load percent of drug in the powder.

In a specific example, dry powder from a dry powder inhaler receptacle, e.g., capsule, holding 25 mg nominal powder dose having at 50% L-Dopa load, i.e., 12.5 mg L-Dopa, is administered in a single breath. Based on a conservative 4-fold dose advantage, the 12.5 mg delivered in one breath are the equivalent of about 50 mg of L-Dopa required in oral administration. Several such capsules can be employed to deliver higher doses of L-Dopa. For instance a size 4 capsule can be used to deliver 50 mg of l-Dopa to the pulmonary system to replace (considering the same conservative 4-fold dose advantage) a 200 mg oral dose.

Properties of the particles enable delivery to patients with highly compromised lungs where other particles prove ineffective for those lacking the capacity to strongly inhale, such as young patients, old patients, infirm patients, or patients with asthma or other breathing difficulties. Further, patients suffering from a combination of ailments may simply lack the ability to sufficiently inhale. Thus, using the methods and particles for the invention, even a weak inhalation is sufficient to deliver the desired dose. This is particularly important when using the particles of the instant invention as rescue therapy for a patient suffering from debilitating illness of the central nervous system for example but not limited to migraine, anxiety, psychosis, depression, bipolar disorder, obsessive compulsive disorder (OCD), convulsions, seizures, epilepsy, Alzheimer's, and especially, Parkinson's disease.

The present invention will be further understood by reference to the following non-limiting examples.

EXEMPLIFICATIONS

EXAMPLE 1

In vivo tests were performed to compare oral and tracheal administration of L-Dopa in a rat model. Animals received an IP injection of the peripheral decarboxylase inhibitor carbidopa (Sigma, St. Louis, Mo.) (200 mg/kg) one hour prior to administration of L-Dopa. Under ketamine anesthesia, the animals were divided into two groups. In the first group of animals (N=4), L-Dopa (8 mg) was suspended in saline containing 2% methylcellulose and given via oral gavage. In the second group (N=5) a small tracheotomy was performed to permit placement of a pipette tip with a modified 2 mm opening through the trachea and into the lungs. The pipette tip was pre-loaded with powdered L-Dopa (8 mg) and was interfaced with an oxygen tank using silicone tubing. Coinciding with the respiratory cycle of the animal, L-Dopa was pushed into the lungs using a burst of oxygen (5 liters/minute). Blood samples (200 $\mu$l) were withdrawn from a previously placed femoral cannula at the following time points: 0 (immediately prior to L-Dopa administration), 1, 5, 15, 30, 45 and 60 minutes following L-Dopa administration.

Figure 1B:
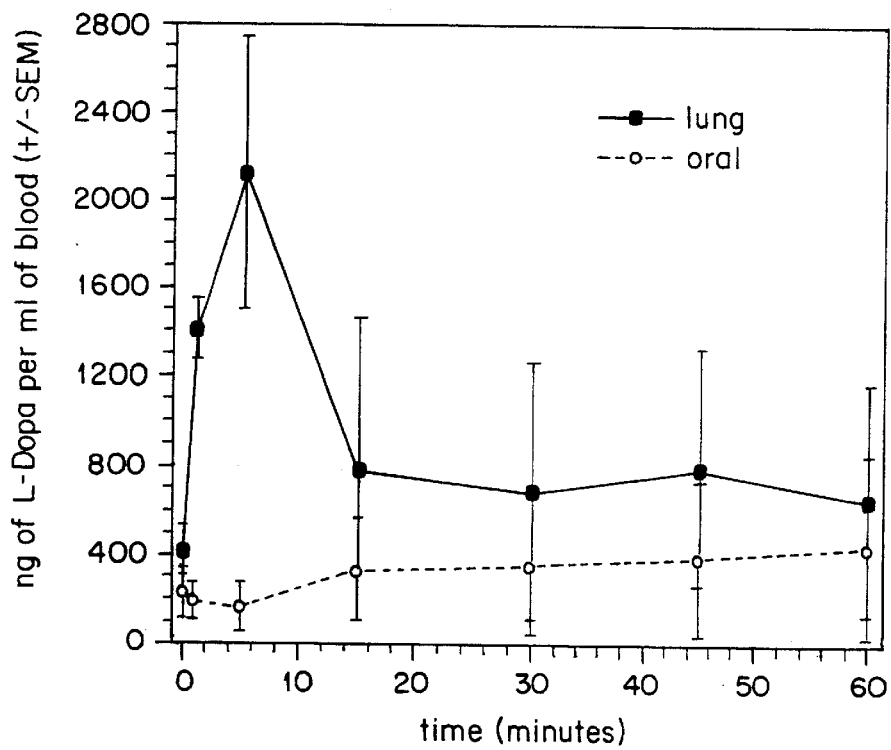

Blood levels of L-Dopa, measured, respectively, by mass spectrometry or HPLC, following administration via oral gavage or direct administration into the lungs are shown in FIGS. 1A and 1B. The increase in blood levels of L-Dopa over time following oral administration was modest. In contrast, administration into the lungs produced a robust and rapid rise in L-Dopa levels which peaked between 1 and 5 minutes post drug administration. L-Dopa levels in this group decreased between 5 and 15 minutes and remained stable thereafter. Data are presented as the mean±SEM ng L-Dopa level/ml blood.

Figure 2A:
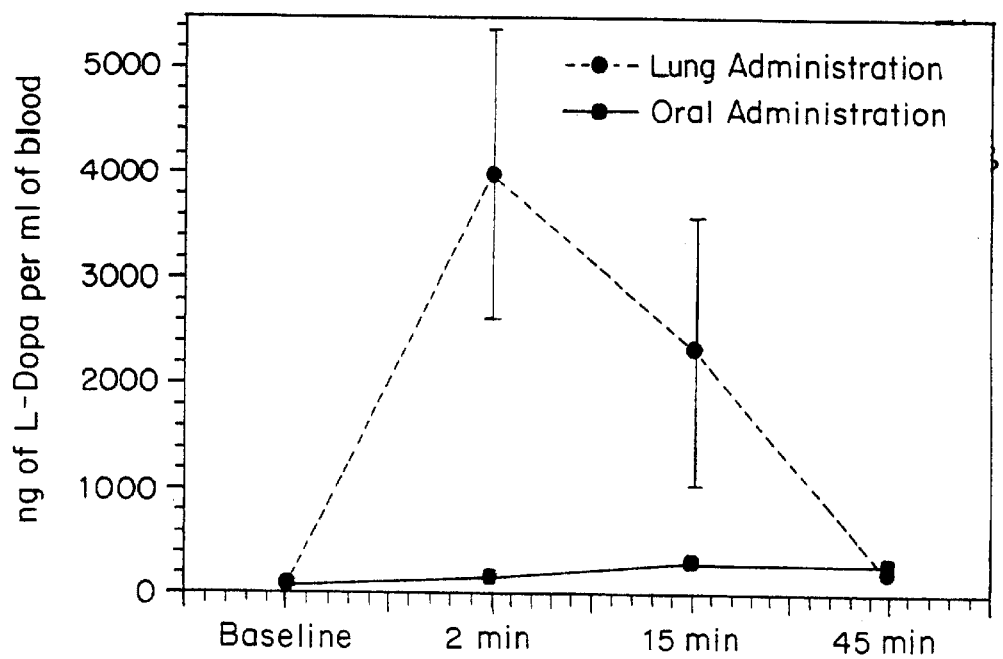

Relationship between blood L-Dopa levels and striatal dopamine levels following delivery of L-Dopa either orally or directly into the lungs, as described above, are shown in FIGS. 2A and 2B. FIG. 2A shows blood L-Dopa levels immediately prior to L-Dopa (baseline) and at 2, 15 and 45 minutes following L-Dopa (N=4–6 per time point for each group). Once again, the levels following administration into the lungs show a robust and rapid increase in L-Dopa levels, relative to the modest increases following oral administration.

Figure 2B:
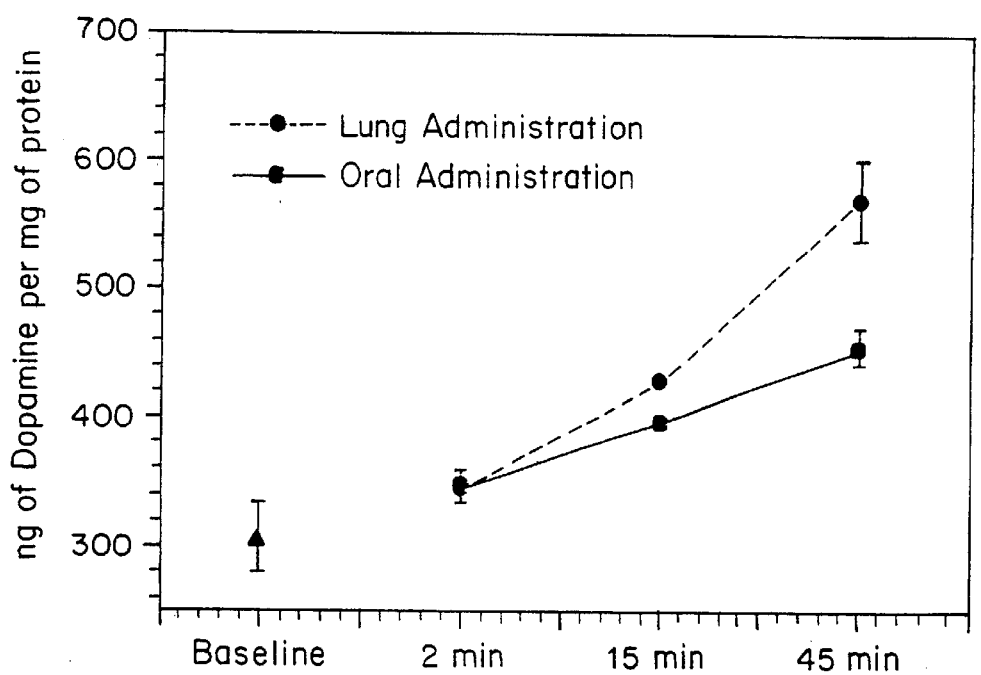

FIG. 2B shows dopamine levels in the striatum from the same animals shown in FIG. 2A. Immediately following withdrawal of the blood sample, the brains were removed and striatum dissected free. Tissue levels of dopamine were determined using high performance liquid chromatography (HPLC). Note that the marked difference in blood L-Dopa levels seen between the two treatments at two minutes was followed, later in time, by more modest but significant differences in striatal levels of dopamine. Blood levels are presented as the mean±SEM ng L-Dopa levels/ml blood. Striatal levels of dopamine are presented as the mean±SEM ng dopamine/mg protein.

Blood and striatal levels of $^{14}C$ following administration of $^{14}C$-L-Dopa as generally described above were also determined and are shown in FIG. 3. A total of 25 $\mu$Ci of radiolabeled L-Dopa was mixed with unlabelled L-Dopa to provide a total drug concentration of 8 mg/rat. Blood samples were taken at 2, 5 and 15 minutes post drug administration L-Dopa (N=6 per time point for each group). At 5 or 15 minutes post L-Dopa, the striatum was removed and both the blood and tissues samples were assayed for $^{14}C$ levels using scintillation. The zero minute plasma values are deduced from other many studies using radioactive agents.

Once again, a robust and rapid increase in plasma levels was achieved via the pulmonary route, which was reflected in increased dopamine activity in the brain at both the 5 minute and 15 minute time points (relative to oral administration).

Figure 4:
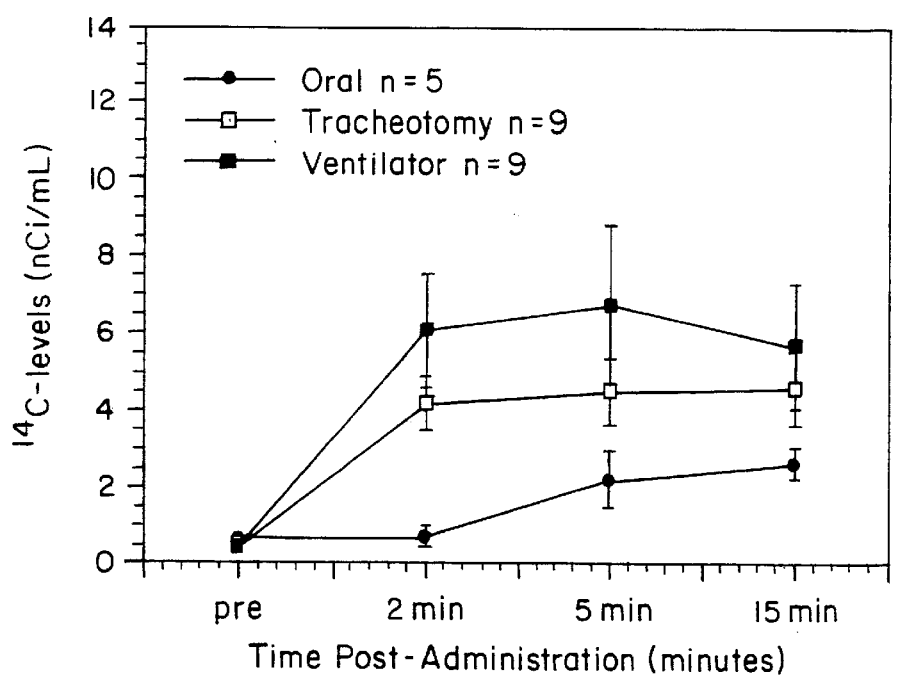
Figure 5:
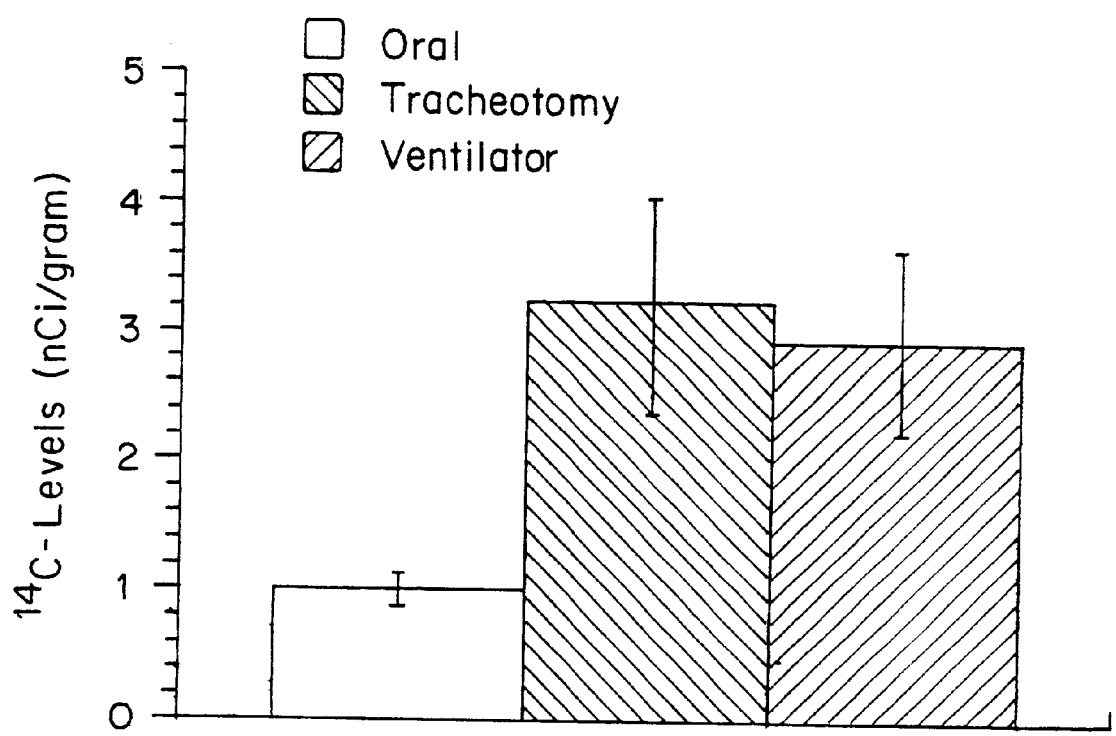
Figure 6A:
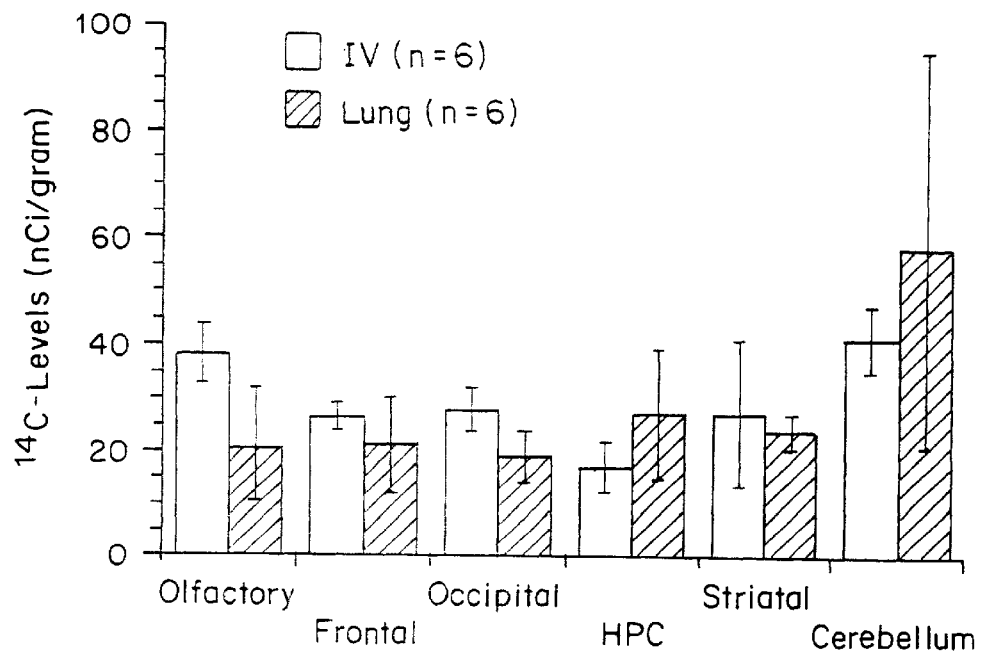
Figure 6B:
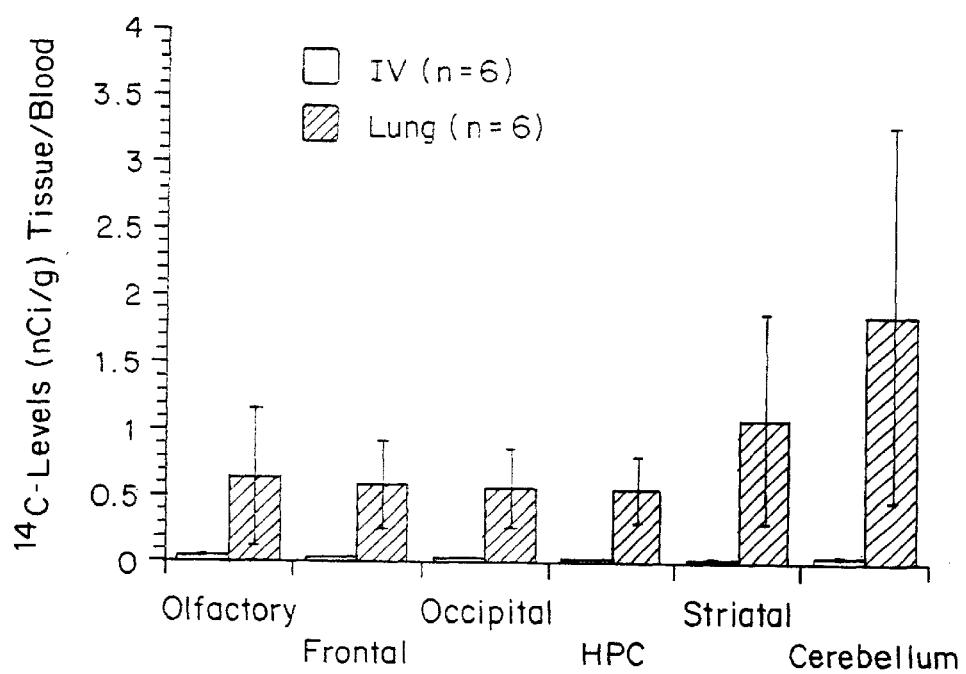
Figure 7A:
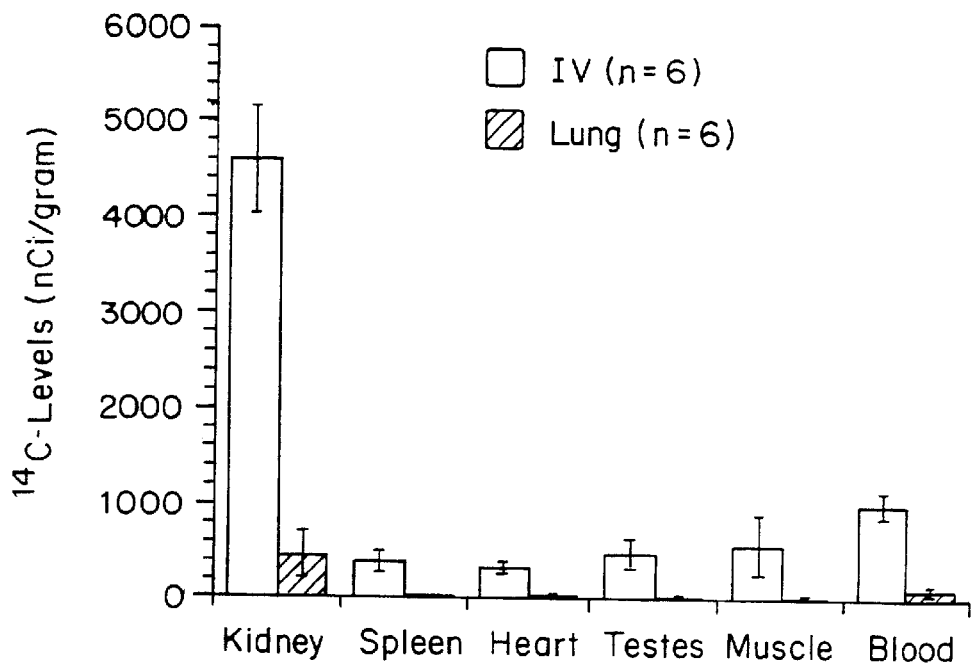
Figure 7B:
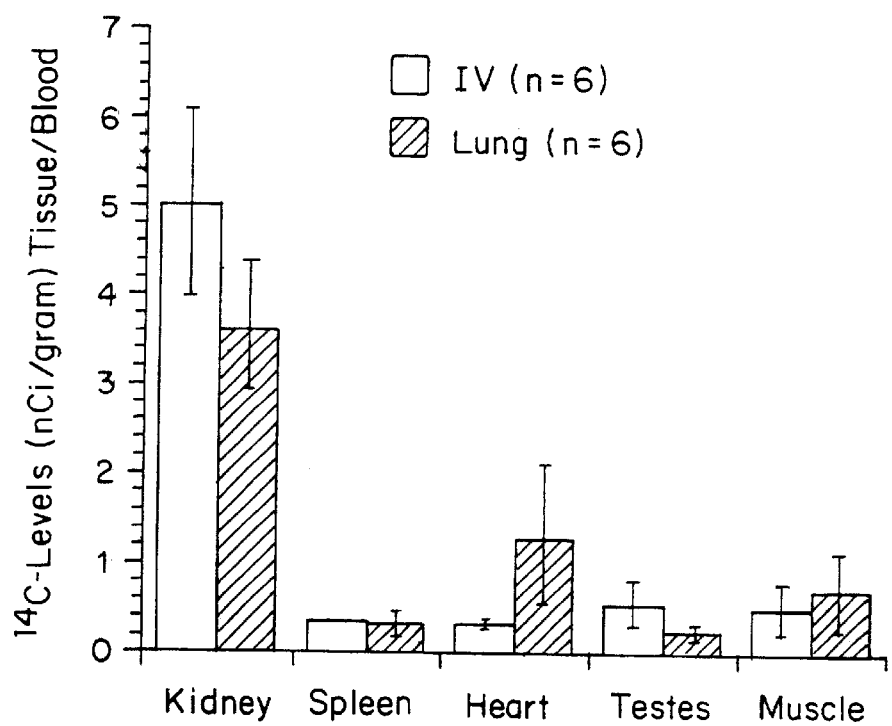

Direct comparison of plasma $^{14}C$ following administration of $^{14}C$-L-Dopa via oral gavage, inhalation using a tracheotomy (as described above) or ventilator (Harvard Apparatus, Inc., Holliston, Mass.) is shown in FIG. 4. Corresponding brain $^{14}C$-L-Dopa levels are shown in FIG. 5. All animals were briefly anesthetized using 1% Isoflurane and immobilized in a harness to allow blood removal via a previously placed femoral cannula. Blood samples were removed at 0, 2, 5, and 15 minutes post administration. For L-Dopa administration using the ventilator, a 24 gauge catheter was placed within the trachea and the L-Dopa (25 $\mu$Ci) was administered over a 3–5 second period using a tidal volume of 1 ml and 100 strokes/minutes. Striatal tissue samples were processed for determinations of levels of radioactivity using scintillation counts. Both the plasma and brain levels of $^{14}C$ were comparably elevated using both the conventional tracheotomy methods and the ventilator.

EXAMPLE 2

Blood, brain and peripheral organ levels of $^{14}C$ were determined following administration of $^{14}C$-Carboplatin via either IV or pulmonary administration. A total of 100 $\mu$Ci of radiolabeled carboplatin was mixed with unlabelled carboplatin to provide a total drug concentration of 8 mg/rat. All animals were anesthetized using ketamine. For IV administration, carboplatin was administered via a previously placed femoral cannula. For pulmonary administration, a 24 gauge catheter was placed within the trachea and the carboplatin was administered using a Harvard ventilator over a 3–5 second period using a tidal volume of 1 ml and 100 strokes/minutes. Blood samples were taken at 10 minutes post drug administration (N=6 per time point for each group). Brains were removed and dissected into various regions including the olfactory, frontal, and occipital cortices, the hippocampus, striatum, and cerebellum. Peripheral organs included the kidneys, spleen, heart, testes, and muscle. All samples were then processed for determinations of $^{14}C$ levels using scintillation.

Results are shown in Table 2, which shows scintillation counts of $^{14}C$-levels in plasma, brain and peripheral organs following $^{14}C$-carboplatin (100 $\mu$Ci/8 mg) administration, and in FIGS. 6A–6B and 7A–7B. Absolute plasma levels of $^{14}C$ were higher following IV administration. However, the absolute brain levels were comparable suggesting that delivery to the brain at this time point was relatively selective. This point is clearer when the ratio of brain to blood $^{14}C$ levels was calculated. Following pulmonary delivery, $^{14}C$ levels were 2833% higher than observed following IV administration. Absolute levels of $^{14}C$ in peripheral tissue was also lower following pulmonary administration (92% lower relative to IV). In contrast to the large differences in selectivity seen in the brain, the relative peripheral selectivity (derived from dividing the levels of radioactivity in peripheral organs by that in the blood) was only 47% higher in the pulmonary group. Interestingly though, the highest levels of $^{14}C$ in peripheral tissue were found in the heart. Together, these data suggest that the brain and the heart may represent sites of preferential delivery at time point immediately following pulmonary drug administration.

TABLE 2

|  |  | 10 Minutes |
|---|---|---|
| Plasma Levels | IV | 994.348 |
|  | Lung | (n = 6) |
|  | (% Difference) | 102.215 |
|  |  | −89.72% |
|  |  | (n = 6) |
| Absolute Brain Levels | IV | 29.47 |
| (nCi/gram) | Lung | 27.29 |
| Relative Brain | IV | 0.03 |
| Selectivity | Lung | 0.88 |
| (Brain/Blood) | (% Difference) | +2833% |
|  | IV(Br/Bl)/Lung(Br/Bl) |  |
| Absolute Tissue | IV | 0.03 |
| Levels | Lung | 0.88 |
| (Peripheral Organs) | (% Difference) | +2833% |
| *excludes kidney | IV(Br/Bl)/Lung(Br/Bl) |  |
| Relative Peripheral | IV | 0.44 |
| Selectivity | Lung | 0.65 |
| (Peripheral/Blood) | (% Difference) | +47.727% |
| *excludes kidney | IV(Per/Bl)/Lung(Per/Bl) |  |

EXAMPLE 3

Particles comprising L-Dopa and suitable for inhalation were produced as follows. 2.00123 g DPPC (Avanti Polar Lipids, Lot #G160PC-25) was added to 2.80 L of ethanol and stirred to dissolve. 0.0817 g L-Dopa (Spectrum, Lot 0Q0128, Laguna Hills, Calif.), 0.9135 g Sodium Citrate (Dehydrate) (Spectrum Lot NX0195), and 0.5283 g Calcium Chloride (Dehydrate) (Spectrum Lot NT0183) were added to 1.2 L of water and dissolved. The solutions were combined by adding the water solution to the ethanol solution and then the solutions were allowed to stir until the solution was clear. The weight percent of the formulation was approximately: 20% L-Dopa, 50% DPPC, 20% Sodium Citrate, 10% Calcium Chloride.

The final solution was then spray dried in a Niro dryer (Niro, Inc., Columbus, Md.) using a rotary atomizer and nitrogen drying gas following the direction of the manufacturer, using the following spray conditions: $T_{inlet}$=120° C., $T_{outlet}$=54° C., feed rate=65 m/min, heat nitrogen=38 mm $H_2O$, atomizer speed=20,000 rpm (V24 atomizer used).

The resulting particle characteristics were: Mass Median Aerodynamic Diameter (MMAD)=2.141 μm and Volume Median Geometric Diameter (VMGD)=10.51 μm.

Under ketamine anesthesia, six rats received pulmonary administration of the formulation described above (20/50/20/10 L-Dopa/DPPC/Sodium Citrate/Calcium Chloride).

Figure 8:
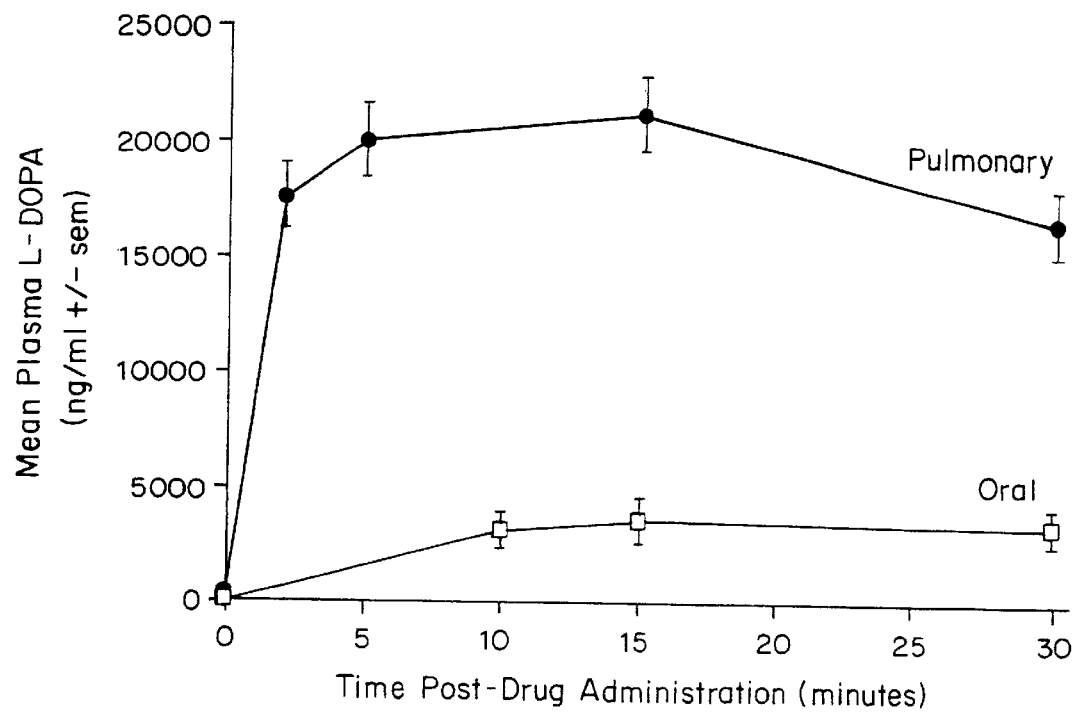

The results are shown in FIG. 8. This FIG. shows blood levels of L-Dopa following administration via oral gavage or direct administration into the lungs via insufflation. L-Dopa levels were measured using both HPLC. Animals received an IP injection of the peripheral decarboxylase inhibitor carbi-dopa (200 mg/kg) 1 hour prior to administration of L-Dopa. Under ketamine anesthesia, the animals were divided into 2 groups. In the first group, animals were fasted overnight and L-Dopa (8 mg) was suspended in saline containing 1% methylcellulose and given via oral gavage. In the second group, insufflation was used to deliver the L-Dopa formulation directly into the lungs. Blood samples (200 μl) were withdrawn from a previously placed femoral cannula at the following time points: 0 (immediately prior to L-Dopa administration), 2, 5, 15, and 30 minutes following L-Dopa administration. The increase in blood levels of L-Dopa over time following oral administration was modest. In contrast, administration into the lungs produced a robust and rapid rise in L-Dopa levels. L-Dopa levels in this group remained elevated relative to oral delivery at 30 minutes post drug administration. Data were normalized to a dose of 8 mg/kg (the total oral gavage dose). Data are presented as the mean (±SEM) ng L-Dopa/ml blood.

EXAMPLE 4

Ketoprofen/DPPC/maltodextrin particles were prepared and administered in vivo.

Ketoprofen (99.5%) was obtained from Sigma, (St. Louis, Mo.), dipalmitoyl phosphatidyl choline (DPPC) from Avanti Polar Lipids, (Alabaster, Ala.) and maltodextrin,M100 (Grain Processing Corp., Muscatine, Iowa).

To prepare ketoprofen/DPPC/Maltodextrin solutions, maltodextrin (0.598 g) was added to 0.60 L USP water. DPPC (0.901 g) was added to 1.40 L ethanol and stirred until dissolved. The water and ethanol solutions were combined, resulting in a cloudy solution. 500 ml of this stock solution was used for each run. The addition of ketoprofen to the DPPC/Maltodextrin stock solution is described in Table 3.

A Niro Atomizer Portable Spray Dryer (Niro, Inc., Columbus, Md.) was used to produce the dry powders. Compressed air with variable pressure (1 to 5 bar) ran a rotary atomizer (2,000 to 30,000 rpm) located above the dryer. Liquid feed of the ketoprofen/DPPC/Maltodextrin solutions, with varying rate (20 to 66 ml/min), was pumped continuously by an electronic metering pump (LMI, model #A151-192s) to the atomizer. Both the inlet and outlet temperatures were measured. The inlet temperature was controlled manually; it could be varied between 100° C. and 400° C., with a limit of control of 5° C. The outlet temperature was determined by the inlet temperature and such factors as the gas and liquid feed rates; it varied between 50° C. and 130° C. A container was tightly attached to the 6" cyclone for collecting the powder product. The spraying conditions for each solution is given in Table 4, which shows that the spraying conditions were held nearly constant throughout the study. The total recovery and yield for each solution is given in Table 5.

The particles were characterized using the Aerosizer (TSI, Inc., Amherst, Mass.) and the RODOS dry powder disperser (Sympatec Inc., Princeton, N.J.) as instructed by the manufacturer. For the RODOS, the geometric diameter was measured at 2 bars. The material from run #5 was also characterized using a gravimetric collapsed Andersen Cascade Inpactor (ACI, 2 stage, Anderson Inst., Sunyra, Ga.). The samples were examined using a scanning electron microscope (SEM).

Table 5 indicates that increasing the weight % of ketoprofen led to a decrease in yield. The addition of ketoprofen to the stock solution linearly decreased yield. This may be due to a decrease in melting temperature for DPPC when mixed with ketoprofen, leading to the yield loss.

Table 6 shows that the particles ranged in diameter from 8.8 μm to 10.2 μm (VMGD) and from 2.65 μm to 3.11 μm (MMAD). The lowest MMAD particles were for the 8.4% loading material (run #5).

Table 7 shows the results of a Andersen Collapsed Impactor study (ACI, gravimetric, n=2) of the material from run #5, the 8.4% loading material. The fine particle fractions (FPF) below 5.6 μm and below 3.4 μm are consistent with powders expected to be respirable.

TABLE 3

| Sample ID | Ketoprofen added (mg) | Total solids (g/L) | % Ketoprofen |
|---|---|---|---|
| Run #1 | 0 | 1.000 | 0 |
| Run #2 | 8.0 | 1.016 | 1.6 |
| Run #3 | 15.1 | 1.030 | 3.0 |
| Run #4 | 30.1 | 1.060 | 5.7 |
| Run #5 | 46.0 | 1.092 | 8.4 |
| Run #6 | 63.0 | 1.126 | 11.2 |

TABLE 4

| Sample ID | Temperature (°C.) Inlet | Temperature (°C.) Outlet | Liquid Feed (ml/min) | Gas Pressure (mm H$_2$O) | Rotor Speed (RPM) | Inlet Dew-point (°C.) |
|---|---|---|---|---|---|---|
| Run #1 | 115 | 36 | 75 | 40 | 18,600 | −27.0 |
| Run #2 | 113 | 38 | 85 | 40 | 18,400 | −26.8 |
| Run #3 | 110 | 38 | 85 | 39 | 18,300 | −26.4 |
| Run #4 | 110 | 39 | 85 | 38 | 18,400 | −25.9 |
| Run #5 | 110 | 38 | 86 | 39 | 18,400 | −25.4 |
| Run #6 | 110 | 38 | 85 | 38 | 18,400 | −25.0 |

TABLE 5

| Sample ID | Weight Collected (mg) | Theoretical Yield (mg) | Actual Yield (% Theoretical) |
|---|---|---|---|
| Run #1 | 186 | 500 | 37.2 |
| Run #2 | 195 | 508 | 38.4 |
| Run #3 | 147 | 515 | 28.5 |
| Run #4 | 127 | 530 | 24.0 |
| Run #5 | 89 | 546 | 16.3 |
| Run #6 | 67 | 563 | 11.9 |

TABLE 6

| Sample ID | MMAD (μm) | Std Dev | MGVD (μm, 2 bar) |
|---|---|---|---|
| Run #1 | 3.11 | 1.48 | 9.0 |
| Run #2 | 3.01 | 1.37 | 9.3 |
| Run #3 | 2.83 | 1.40 | 10.3 |
| Run #4 | 2.84 | 1.41 | 10.4 |
| Run #5 | 2.65 | 1.39 | 9.8 |
| Run #6 | 2.83 | 1.38 | 8.8 |

TABLE 7

| | |
|---|---|
| Stage 0 | 1.33 mg |
| Stage 2 | 2.75 mg |
| Stage F | 3.17 mg |
| Capsule Fill | 12.37 mg |
| Weight < 5.6 μm | 5.92 |
| FPF$_{5.6}$ | 0.479 |
| Weight < 3.4 μm | 3.17 |
| FPF$_{3.4}$ | 0.256 |

350 mg of particles containing 8% ketoprofen in 60/40 DPPC/maltodextrin were produced as described above and administered to 20 Sprague Dawley rats. Each of 8 rats were given 7 mg of powder via insufflation, and each of 7 rats were orally given 7 mg of powder dissolved in 50% ethanol. Time points were set at 0, 5, 15, 30, 60, 120, 240, 360 and 480 minutes. For t=0, 4 animals were tested without dosing. For each time point after, samples were taken from either 3 or 4 rats. Each rat was used for 4 time points, with 3 or 4 animals each in four groups. The animals were distributed as follows: 3 animals oral at 5, 30, 120, 360 minutes; 4 animals insufflation at 15, 60, 240, 480 minutes. Sufficient blood was drawn at each time point for the ketoprofen plasma assay. Blood samples were centrifuged, the plasma collected and then frozen at −20° C. prior to shipment to the contract laboratory for analysis. The assay used in this study has a lower detection limit of 1.0 mg/ml.

Rats were dosed with ketoprofen via either oral or pulmonary administration to determine if the pulmonary route would alter the time required to achieve maximum plasma concentration. The results (FIGS. 9–11) show that the pulmonary delivery route leads to a very rapid uptake with $C_{max}$ occurring at ≦10 minutes. The rats that received oral doses of ketoprofen displayed somewhat anomalous pharmacokinetic behavior, with the relative bioavailability being about half of that displayed for rats dosed via the pulmonary route. This result was unexpected as ketoprofen is 90% orally bioavailable in the human model. This anomaly for the orally dosed rats does not, however, invalidate the significance of the early $C_{max}$ seen for the rats dosed via the pulmonary route.

Figure 9:
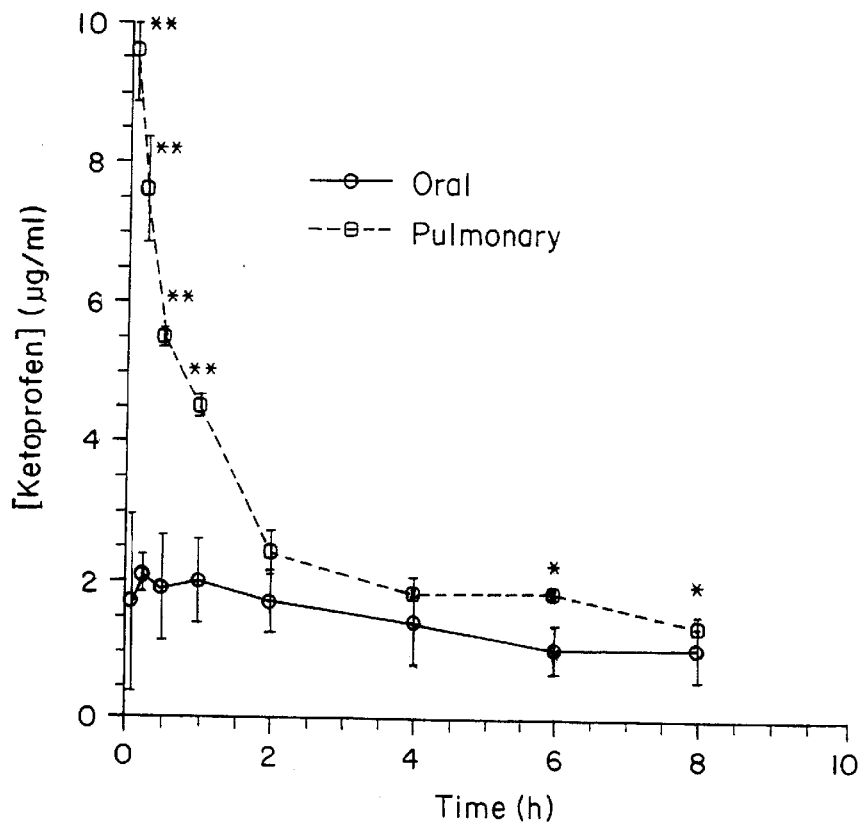
Figure 10:
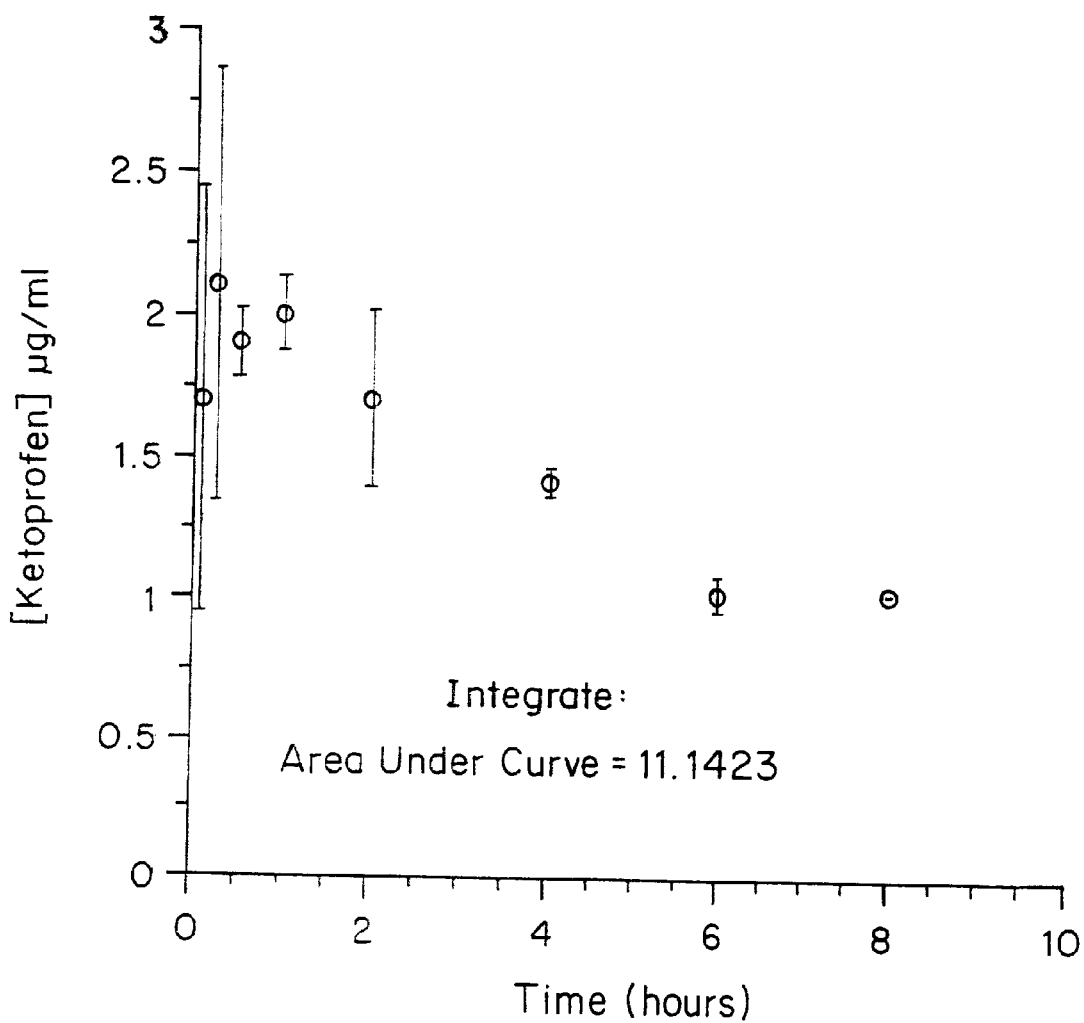
Figure 11:
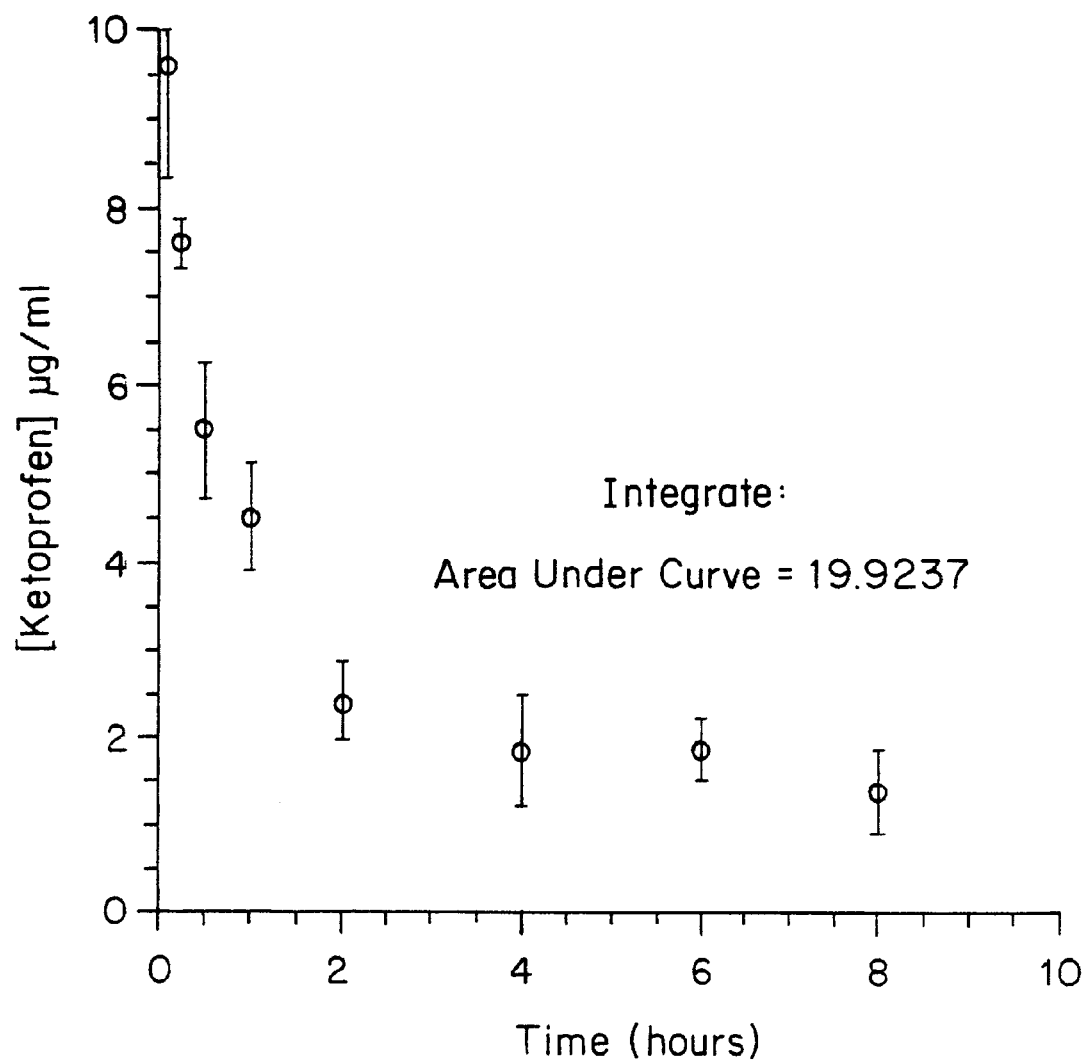
Figure 12:
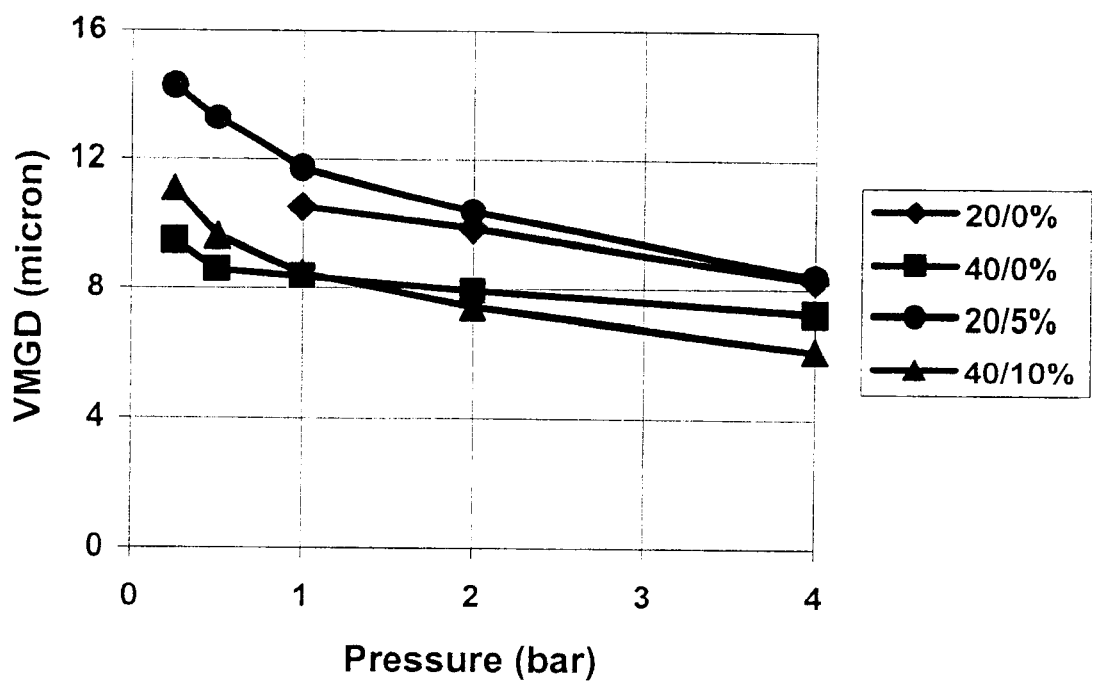
Figure 13A:
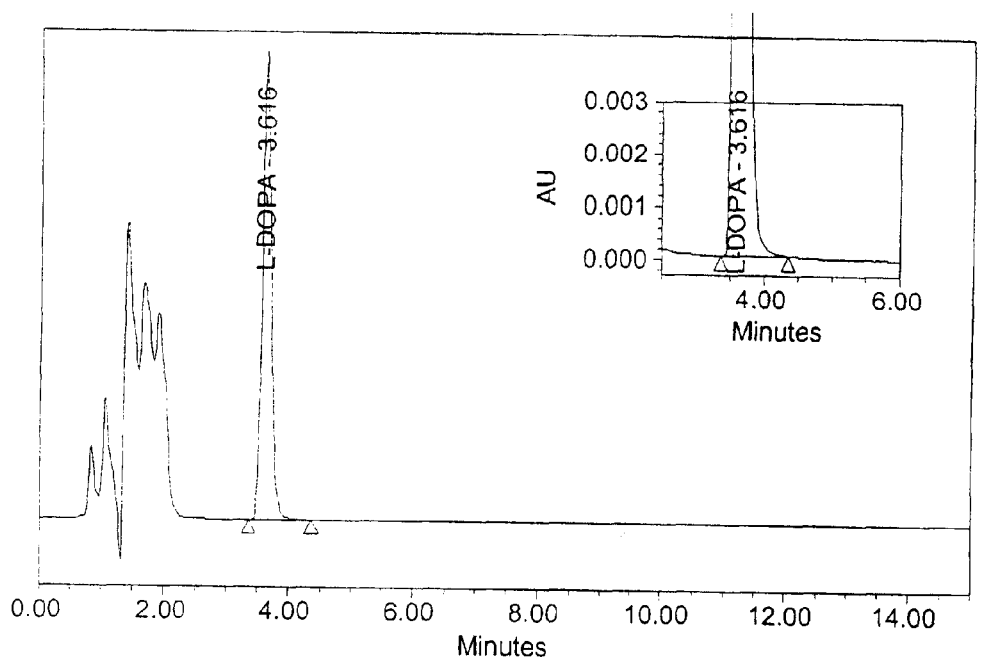
Figure 13B:
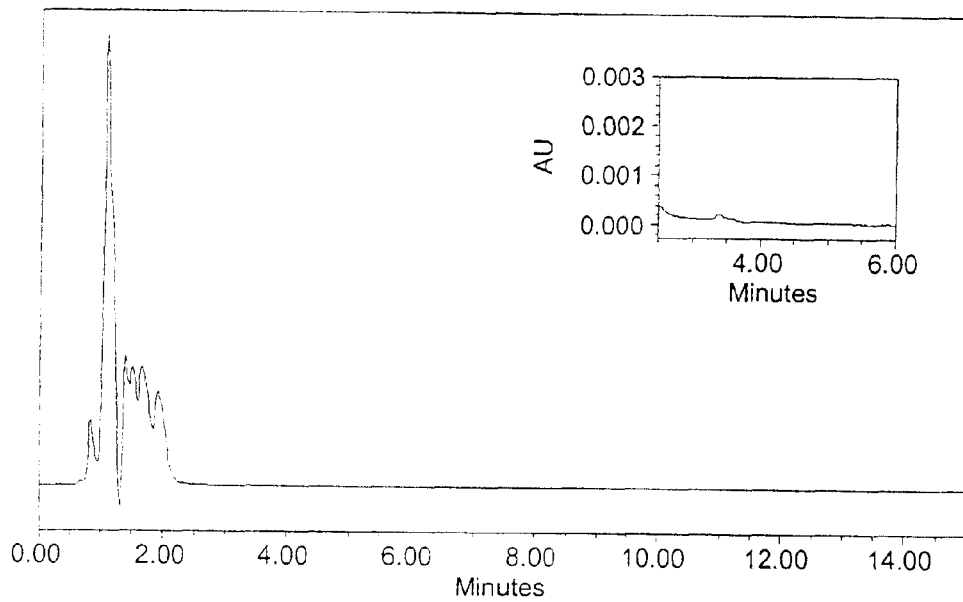

The results are provided in Table 8. The averages were calculated along with the standard errors and p values. The results are also presented graphically in FIGS. 9–11, wherein FIG. 9 shows both data sets, FIG. 10 gives the oral dosing results and FIG. 11 shows the insufflation results. For FIG. 9, points with p<0.05 are marked with "*" and points with p<0.01 are marked with "**". For FIGS. 10 and 11, AUC (area under the curve) was performed via numerical integration of the curve with smooth interpolation.

At t=0, all rats showed ketoprofen levels below the detection limit for the assay. From t=5 min to t=60 min, the insufflated rats had significantly higher plasma levels of ketoprofen. At t=120 min and t=240 min, the plasma levels of ketoprofen of the two groups were statistically equivalent. At t=360 min and t=480, the plasma levels of ketoprofen for both groups approached the detection limit for the assay.

The ratio of the AUCs for insulflated rats vs. orally dosed was about 2. The plasma concentrations for ketoprofen at the early time points were statistically significant as well.

$C_{max}$ for the insufflated rats clearly occurred at <15 min and $C_{max}$ for the orally dosed rats occurred between 15–60 min. Due to the large standard error and the relatively low plasma levels for this group, it is not possible to accurately determine the time required for Cmax.

Pulmonary administration resulted in Cmax occurring very quickly (<15 min) compared to oral dosing (t=15 to 60 min).

The insufflated rats showed higher bioavailability compared to the orally dosed rats. This is unexpected as previous studies have shown ketoprofen to have consistently high (>90%) bioavailability in humans when dosed orally, subcutaneously or rectally. Since the pharmokinetic behavior of ketoprofen delivered orally is well-known, the anomalous results seen here for the orally dosed group do not invalidate the results seen for the insufflation group.

TABLE 8

| Time Min. | Oral Dosing Avg. (ug/ml) | Group St. Dev. | Pulmonary Avg. (ug/ml) | Dosing Group Std. Dev. | P Value |
|---|---|---|---|---|---|
| 0 | 1.0 | N/A | 1.0 | N/A | |
| 5 | 1.7 | 0.75 | 9.6 | 1.27 | 0.0003 |
| 15 | 2.1 | 0.76 | 7.6 | 0.28 | 0.0000 |
| 30 | 1.9 | 0.12 | 5.5 | 0.76 | 0.0012 |

TABLE 8-continued

| Time Min. | Oral Dosing Avg. (ug/ml) | Group St. Dev. | Pulmonary Avg. (ug/ml) | Dosing Group Std. Dev. | P Value |
|---|---|---|---|---|---|
| 60 | 2.0 | 0.13 | 4.5 | 0.60 | 0.0002 |
| 120 | 1.7 | 0.31 | 2.4 | 0.44 | 0.0929 |
| 240 | 1.4 | 0.05 | 1.8 | 0.63 | 0.2554 |
| 360 | 1.0 | 0.06 | 1.8 | 0.35 | 0.0224 |
| 480 | 1.0 | 0.00 | 1.3 | 0.47 | 0.2174 |

Average plasma levels of Ketoprofen from oral and pulmonary group

EXAMPLE 5

The following experimental methods and instrumentation were employed to determine the physical characteristics of particles including L-DOPA and suitable for pulmonary delivery.

Aerodynamic diameter was analyzed using the API Aero-Disperser and Aerosizer (TSI, Inc., St. Paul, Minn.) following standard procedures (Alkermes SOP# MS-034-005). Sample powder was introduced and dispersed in the Aero-Disperser and then accelerated through a nozzle in the Aerosizer. A direct time-of-flight measurement was made for each particle in the Aerosizer, which was dependent on the particle's inertia. The time-of-flight distribution was then translated into a mass-based aerodynamic particle size distribution using a force balance based on Stokes law.

Geometric diameter was determined using a laser diffraction technique (Alkermes SOP# MS-021-005). The equipment consists of a HELOS diffractometer and a RODOS disperser (Sympatec, Inc., Princeton, N.J.). The RODOS disperser applies a shear force to a sample of particles, controlled by the regulator pressure of the incoming compressed air. The dispersed particles travel through a laser beam where the resulting diffracted light pattern produced is collected by a series of detectors. The ensemble diffraction pattern is then translated into a volume-based particle size distribution using the Fraunhofer diffraction model, on the basis that smaller particles diffract light at larger angles.

The aerodynamic properties of the powders dispersed from the inhaler device were assessed with a 2-stage MkII Anderson Cascade Impactor (Anderson Instruments, Inc., Smyrna, Ga.). The instrument consists of two stages that separate aerosol particles based on aerodynamic diameter. At each stage, the aerosol stream passes through a set of nozzles and impinges on the corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain.

Prior to determining the loading of drug within a dry powder, the drug had to be first be separated from the excipients within the powder. An extraction technique to separate L-Dopa from the excipient DPPC was developed. Particles were first dissolved in 50% chloroform/50% methanol. The insoluble L-Dopa was pelleted out and washed with the same solvent system and then solubilized in 0.5 M hydrochloric acid. DPPC was spiked with L-DOPA to determine recovery. Samples were injected onto a reverse phase high pressure liquid chromatography (HPLC) for analysis.

Separation was achieved using a Waters Symmetry C18 5-μm column (150-mm×4.6-mm ID). The column was kept at 30° C. and samples were kept at 25° C. Injection volume was 10 μL. The mobile phase was prepared from 2.5% methanol and 97.5% aqueous solution (10.5 g/L citric acid, 20 mg/L EDTA, 20 mg/L 1-octanesulfonic acid sodium salt monohydrate). Mobile phase was continually stirred on a stir plate and degassed through a Waters in-line degassing system. L-Dopa was eluted under isocratic conditions. Detection was performed using an ultraviolet detector set at wavelength 254 nm.

Since the average single oral dose of L-Dopa generally ranges from 100–150 mg, experiments were conducted to prepare particles suitable for inhalation which included high loads of L-Dopa. Formulations of 20% and 40% L-Dopa load were studied. Carbidopa, a decarboxylase inhibitor given in conjunction with L-Dopa to prevent peripheral decarboxylation, was also included at a 4:1 weight/weight (w/w) ratio in some of the formulations. L-Dopa and combination of L-Dopa and carbidopa were successfully sprayed with DPPC formulations. The optimal formulation consisted of L-Dopa and/or carbidopa, 20% (w/w) sodium citrate, and 10% (w/w) calcium chloride, and the remainder dipalmitoyl phosphatidyl chlorine (DPPC).

Details on formulations and the physical properties of the particles obtained are summarized in Table 9. The aerodynamic size or the mass median aerodynamic diameter (MMAD) was measured with an Aerosizer, and the geometric size or the volume median geometric diameter (VMGD) was determined by laser diffraction, and the fine particle fraction (FPF) was measured using a 2-stage Andersen Cascade Impactor. As shown in FIG. 12 and by the VMGD ratios in Table 9, the powders were flow rate independent. Scanning electron micrography was employed to observe the particles.

TABLE 9

| L-Dopa/Carbi dopa | | | | | |
|---|---|---|---|---|---|
| Load (%) ID | Yield (%) | VMGD (μm) at 2 bar | VMGD ratio 0.5/4.0 bar | MMAD (μm) | FPF (%) 5.6/3.4 |
| 20/0 | >40 | 9.9 | NA | 2.7 | NA |
| 40/0 | >40 | 8.0 | 1.2 | 3.3 | 42/17 |
| 20/5 | 42 | 10 | 1.6 | 3.1 | 64/38 |
| 40/10 | >20 | 7.4 | 1.6 | 3.8 | 40/14 |

L-Dopa integrity appeared to be preserved through the formulation and spray drying process. L-Dopa was extracted from L-Dopa powders and analyzed by reverse phase HPLC. No impurities were detected in the L-Dopa powders (FIG. 13A); the early peaks eluted around 1–2 minutes are due to solvent as can be seen from FIG. 13B which is a blank sample that did not contain L-Dopa. The purity of L-Dopa recovered from the particles was 99.8% and 99.9% respectively for the 20% and 40% loaded particles.

To determine the loading (weight percent) of L-Dopa within the powder, the L-Dopa was first separated from the excipients in the formulation and then analyzed by reverse phase HPLC. Results of the L-Dopa recovery from the powders and the final load calculations are given in Table 10. Both extraction recoveries and load determination were satisfactory. The determined actual weight percent of L-Dopa in the powder was approximately 87% of the theoretical drug load.

TABLE 10

| Powder Formulation | Extraction recovery % | Actual load (%) |
|---|---|---|
| 20/0 | 100 ± 4.5 | 17.3 ± 0.2 |
| 40/0 | 101 ± 2.8 | 35.0 ± 5.4 |

EXAMPLE 6

Determinations of plasma levels of L-Dopa were made following IV injection, oral gavage, or insufflation into the lungs. Carbidopa generally is administered to ensure that peripheral decarboxylase activity is completely shut down. In this example, animals received an intraperitoneal (IP) injection of the peripheral decarboxylase inhibitor carbidopa (200 mg/kg) 1 hour prior to administration of L-Dopa. Under ketamine anesthesia, the animals were divided into 3 groups. In the first group of animals, L-Dopa (2 mg) was suspended in saline containing 1% methylcellulose and 1% ascorbic acid and given via oral gavage. In the second group, an insufflation technique was used for pulmonary administration of particles including L-Dopa (20% loading density). A laryngoscope was used to visualize the rat's epiglottis and the blunt-tip insufflation device (PennCentury Insufflation powder delivery device) was inserted into the airway. A bolus of air (3 cc), from an attached syringe, was used to delivery the pre-loaded powder from the chamber of the device into the animal's lungs. A total of 10 mg of powder (2 mg L-Dopa) was delivered. In the third group, a previously-placed femoral cannula was used to delivery a bolus (2–3 second) of L-Dopa (2 mg). Blood samples (200 $\mu$L) were withdrawn from each animal using the femoral cannula at the following timepoints: 0 (immediately prior to L-Dopa administration), 2, 5, 15, 30, 60, 120, and 240 minutes following L-Dopa administration. All samples were processed for L-Dopa determinations using HPLC.

Figure 14A:
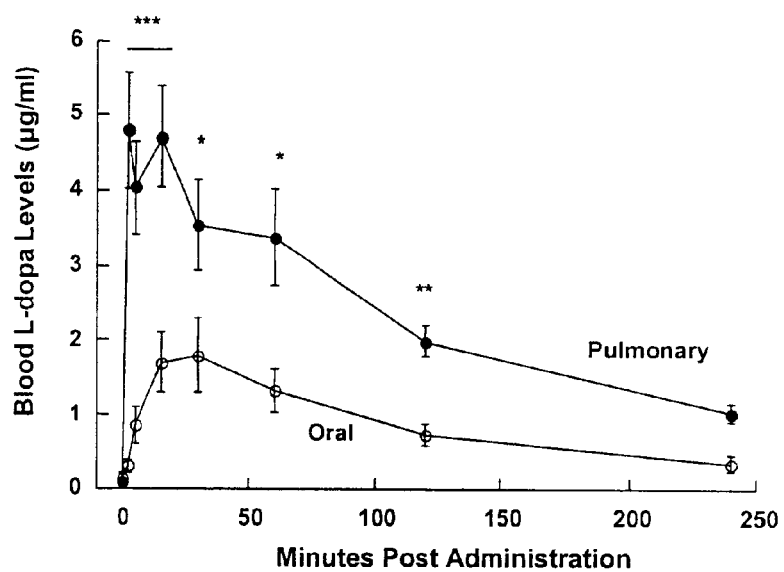
Figure 14B:
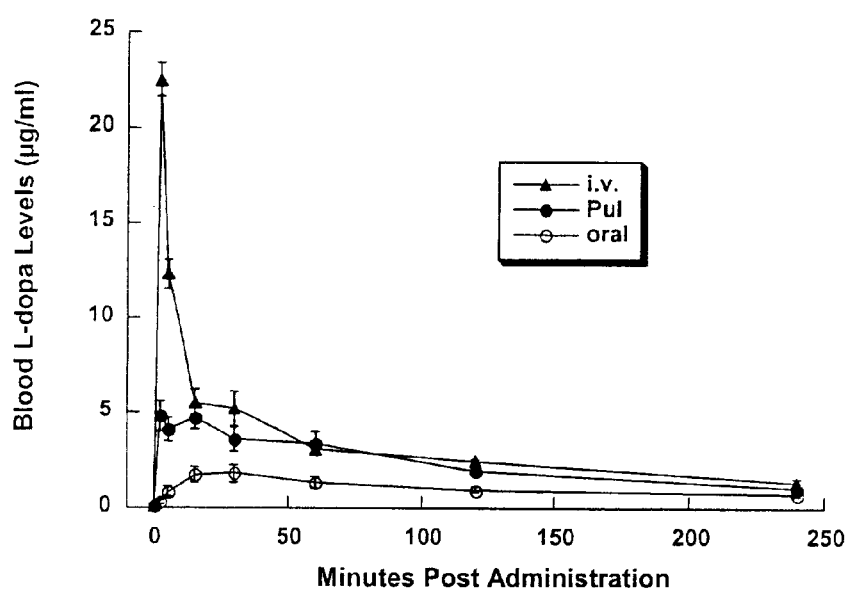

The results of a pharmacokinetic study using the procedure described are shown in FIGS. 14A and 14B. The results of a comparison of pulmonary delivery of L-Dopa with oral administration are depicted in FIG. 14A. Following insufflation, peak plasma levels of L-Dopa were seen at the earliest time point measured (2 minutes) and began to decrease within 15 minutes of administration while still remaining elevated, relative to oral administration, for up to 120 minutes. In contrast, oral administration of L-Dopa resulted in a more gradual increase in plasma L-Dopa levels, which peaked at 15–30 minutes following administration and then decreased gradually over the next 1–2 hours.

Intravenous, oral and pulmonary delivery also were compared. The results are shown in FIG. 14B. This panel depicts the same data presented in FIG. 14A with the addition of the IV administration group which allows direct comparisons of the plasma L-Dopa levels obtained following all three routes of administration (pulmonary, oral, and IV). Data are presented as the mean±SEM $\mu$g L-Dopa/mL blood. Plasma levels of L-Dopa rapidly increased following intravenous (IV) administration. The highest levels of L-Dopa were seen at 2 minutes and decreased rapidly thereafter.

Bioavailability was estimated by performing area under the curve (AUC) calculations. Over the entire time course of the study (0–240 min), the relative bioavailability (compared to IV) of pulmonary L-Dopa was approximately 75% as compared 33% for oral L-Dopa. The relative bioavailability of pulmonary L-Dopa at 15 min and 60 min post administration was 38% and 62%, respectively, while that of oral L-Dopa was 9% and 24%, respectively.

EXAMPLE 7

Pharmacodynamic evaluation of rats receiving L-Dopa also was undertaken. Rats received unilateral injections of the neurotoxin 6-OHDA (specific for dopamine neurons in the brain) into the medial forebrain bundle. Rats were then screened to assure successful striatal dopamine depletion using a standard apomorphine-induced turning paradigm. Beginning two weeks after surgery, animals were tested weekly for three weeks for apomorphine-induced rotation behavior. For this test, animals received an IP injection of apomorphine (0.25 mg/kg for the first test and 0.1 mg/kg for the following two tests) and were placed into a cylindrical Plexiglass bucket. Each 360-degree rotation was counted for 30 minutes and only those animals exhibiting >200 rotations/30 minutes (12/30 lesioned rats) were used in behavioral testing.

The lesioned rats were challenged with several motor tasks post L-Dopa administration. The data from the studies (placing task, bracing task, akinesia) further emphasized the advantage of pulmonary delivery over oral delivery.

In one test, animals passing the apomorphine challenge were tested using a "placing task". Prior to each test day, animals received an IP injection of the peripheral decarboxylase inhibitor carbidopa (200 mg/kg). Animals then received oral L-Dopa (0, 20 or 30 mg/kg) or pulmonary L-Dopa (0, 0.5, 1.0 or 2.0 mg of L-Dopa) and were tested 15, 30 60 and 120 minutes later. Throughout testing with oral and pulmonary delivery of L-Dopa, each animal received every possible drug combination in a randomized fashion.

The pharmacodynamics "placing task" required the animals to make a directed forelimb movement in response to sensory stimuli. Rats were held so that their limbs were hanging unsupported. They were then raised to the side of a table so that their bodies were parallel to the edge of the table. Each rat received 10 consecutive trials with each forelimb and the total number of times the rat placed its forelimb on the top of the table was recorded.

Figure 15A:
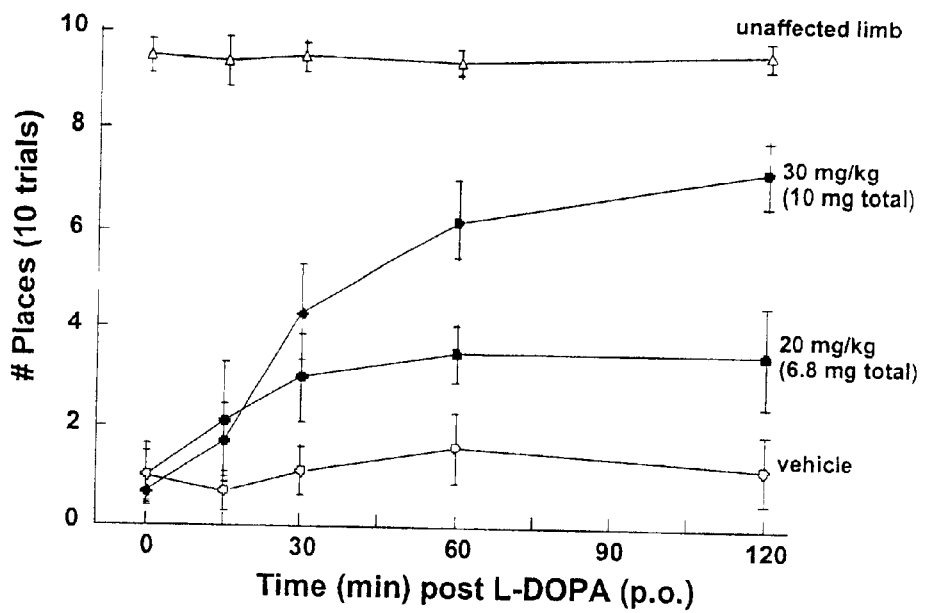
Figure 15B:
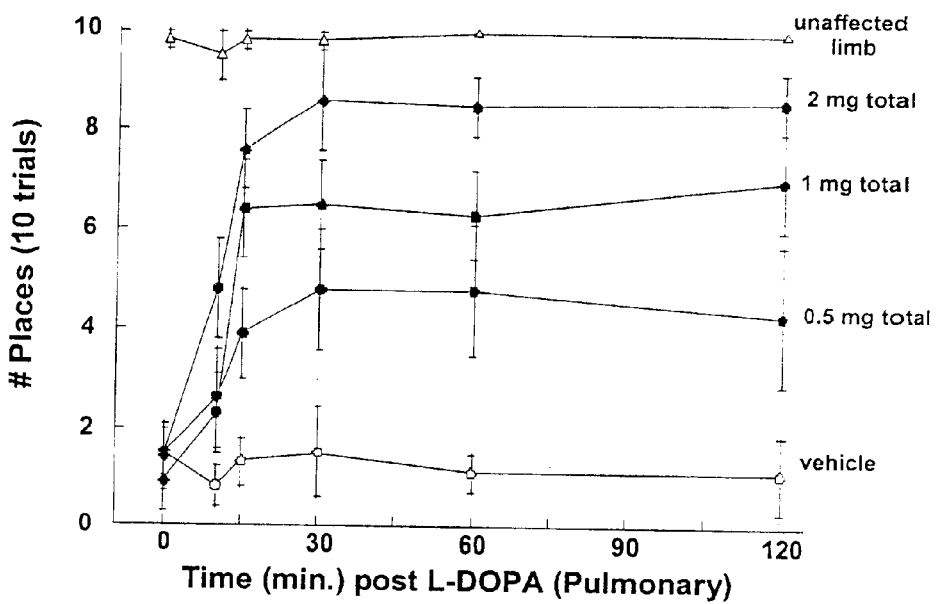

Results from a "placing task" tests are shown in FIGS. 15A and 15B. At baseline (t=0; immediately prior to L-Dopa administration), the animals performed nearly perfectly on this task with the unaffected limb, making greater than 9/10 correct responses. In contrast, the animals were markedly impaired in their ability to perform the same task with the impaired limb, making approximately 1 correct response over the 10 trials.

Oral L-Dopa (FIG. 15A) produced a dose-related improvement in performance with the impaired limb. At the highest dose tested (30 mg/kg), performance was improved, relative to saline control, within 30 minutes and peaked between 1–2 hours after drug administration. The lower dose (20 mg/kg) also improved performance slightly with maximal effects at 60 minutes and stable performance thereafter. No changes were noted following administration of the saline control.

In contrast to oral administration, performance on the "placing task" rapidly improved following pulmonary delivery of L-Dopa, as seen in FIG. 15B. At the highest dose tested, significant improvements occurred within 10 minutes, with peak benefits observed within 15–30 minutes (as opposed to 1–2 hours with oral administration). These effects were dose-related, with significant improvements seen with doses as low as 0.5 mg of L-Dopa. In comparison to the recovery shown with oral delivery, the behavioral improvements were seen with markedly lower total doses using the pulmonary route. For instance, the extent of recovery with 30 mg/kg of L-Dopa given orally was comparable to the recovery seen with 1 mg of L-Dopa given by the pulmonary route (note that 1 mg of pulmonary L-Dopa is equivalent to approximately 3 mg/kg, given that the animals body weight was approximately 300 g). Accordingly, when the L-Dopa doses were normalized by body weight, this represented nearly a 10-fold difference in the drug required to produce equivalent efficacy. Finally, the persistence of the behavioral improvements was comparable using the two delivery routes.

Figure 16A:
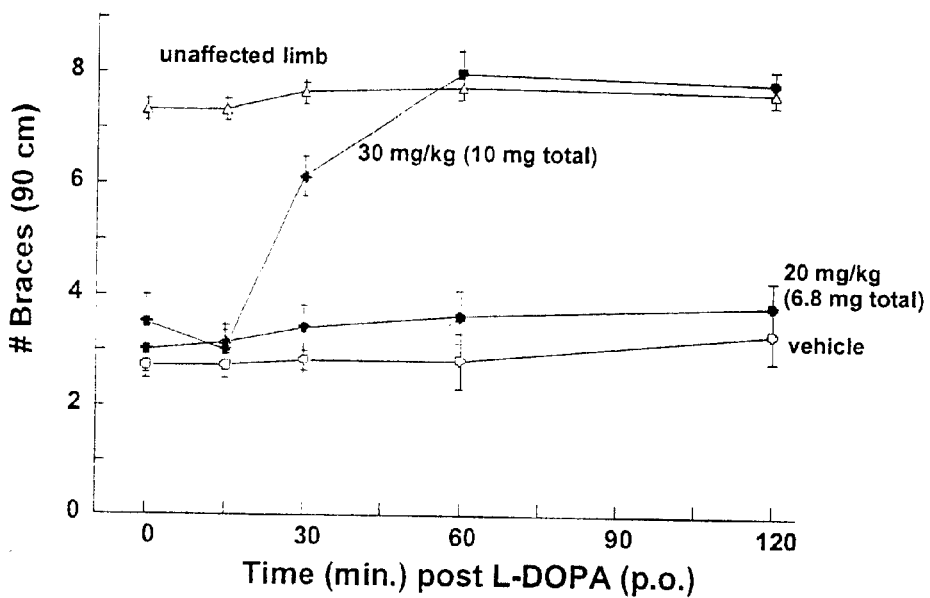
Figure 16B:
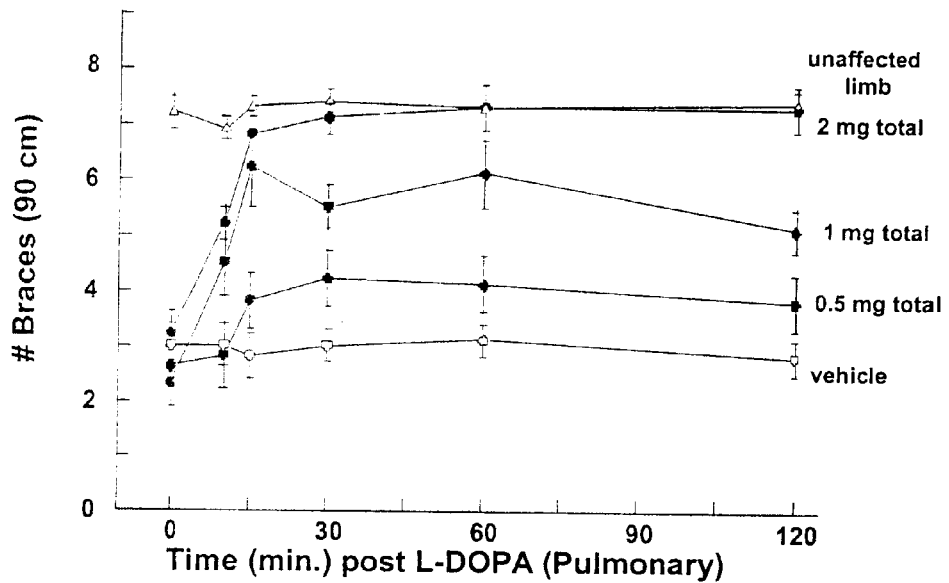

Results from a bracing test are shown in FIGS. 16A and 16B. This test was performed using the same animals and at the same time as the "placing task" test described above. Rats were placed on a smooth stainless steel surface and gently pushed laterally 90 cm at approximately 20 cm/second. The number of steps the rat took with the forelimb on the side in which the rat was moving was recorded. Each trial included moving the rat 2 times in each direction.

The animals demonstrated a profound impairment in their ability to perform this task with the impaired limb, making approximately 3 responses compared to approximately 7 with the unaffected limb, as seen in FIG. 16A. Again, oral administration improved performance on this task in a dose-related manner. Administration of 30 mg/kg (approximately 10 mg L-Dopa) improved performance within 30 minutes. Maximal effects were seen within 60 minutes and remained stable thereafter. A lower dose of oral L-Dopa (20 mg/kg or approximately 7 mg of L-Dopa) slightly improved performance. Again, administration of the saline control did not affect performance.

In contrast to oral administration, performance on this task rapidly improved following pulmonary administration of L-Dopa, as shown in FIG. 16B. Significant improvements were seen within 10 minutes, with peak benefits observed within 15–30 minutes (as opposed to 30–60 minutes with oral administration). These effects were dose-related, with modest, but statistically significant improvements seen with as low as 0.5 mg (equivalent to approximately 1.5 mg/kg). As with the other functional tests, the behavioral improvement achieved following pulmonary L-Dopa occurs at doses far below those required to achieve a similar magnitude of effect following oral delivery. Finally, the persistence of the behavioral improvements was comparable using the two delivery routes.

Figure 17A:
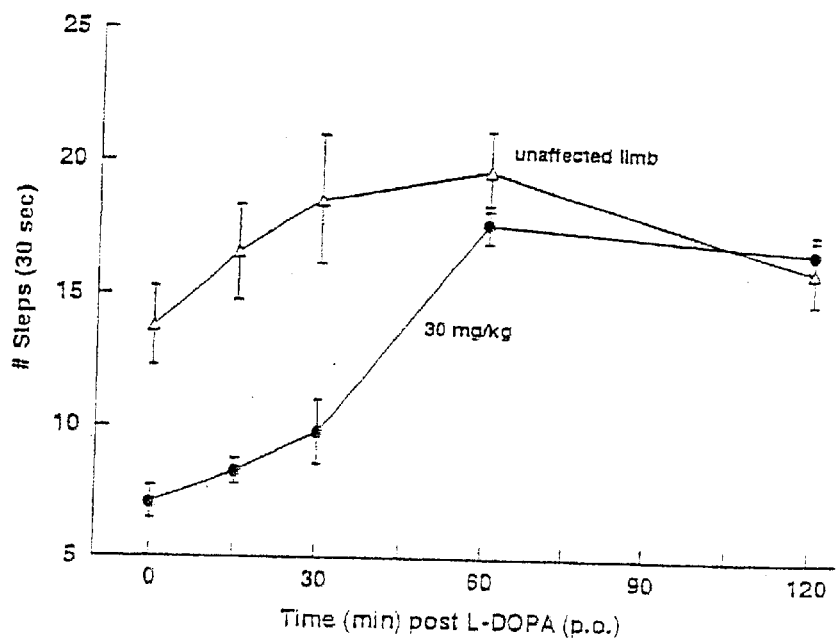
Figure 17B:
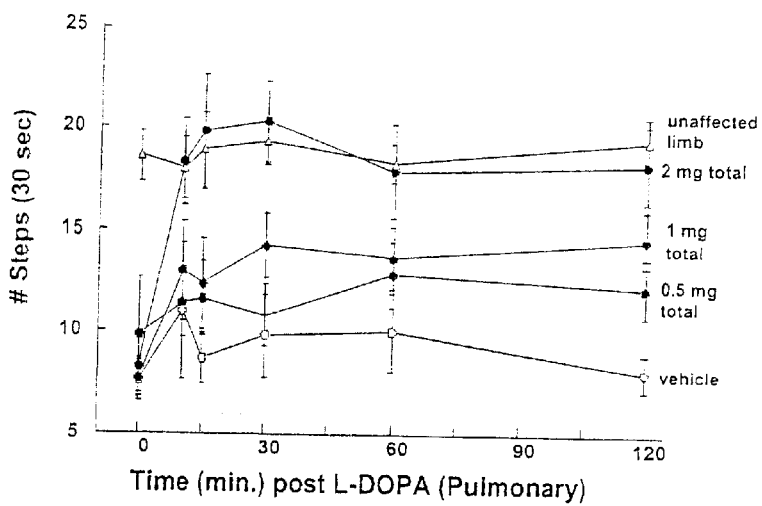

A functional akinesia pharmacodynamics study also was conducted. The results are shown in FIGS. 17A and 17B. This test was performed using the same animals and at the same time as the two preceding tests. In this task, the animal was held so that it was standing on one forelimb and allowed to move on its own. The number of steps taken with the forelimb the rat was standing on was recorded during a 30 second trial for each forelimb.

As was seen with the placing and bracing tests, the animals demonstrated a profound impairment in their ability to perform the akinesia task with the impaired limb. While the animals made approximately 17 steps with the normal limb, they made fewer than half this number with the impaired limb (range=0–10 steps). Oral administration (FIG. 17A) improved performance on this task in a dose-related manner. Administration of 30 mg/kg (approximately 10 mg L-Dopa) improved performance within 30 minutes and maximal effects were seen within 60 minutes. A lower dose of oral L-Dopa (20 mg/kg or approximately 6.8 mg of L-Dopa) produced the same pattern of recovery although the absolute magnitude of improvement was slightly lower than that seen with the higher dose of L-Dopa. Performance remained stable between 60 and 120 minutes following administration of both doses. Administration of the saline control did not affect performance.

In contrast to oral administration, performance on this task rapidly improved following pulmonary administration of L-Dopa, as depicted in FIG. 17B. Significant improvements were seen within 10 minutes, with peak benefits observed within 15–30 minutes (as opposed to 60 minutes with oral administration). These effects were dose-related statistically significant ($p<0.05$) improvements seen with as low as 1.0 mg. As with the other functional tests, the behavioral improvement achieved following pulmonary L-Dopa occurred at doses far below those required to achieve a similar magnitude of effect following oral delivery. Finally, the persistence of the behavioral improvements was comparable using the two delivery routes.

Animals also were tested on a standard pharmacodynamics rotation test known to be a sensitive and reliable measure of dopamine activity in the brain. For this test, animals received either oral L-Dopa (30 mg/kg or approximately 10 mg total) or pulmonary L-Dopa (2 mg total). These doses were chosen for this test because they represent the doses of L-Dopa shown to produce maximal efficacy in the previous functional tests. Following dosing, animals were placed into a cylindrical Plexiglas bucket. Each 360-degree rotation was counted and grouped into 5 minute bins over a 120 minute test period. Animals were also tested for rotation behavior with and without pre-treatment with carbidopa.

All of the animals used in these studies received unilateral injections of 6-OHDA. Because the dopamine depletions are unilateral, the uninjected side remained intact and still able respond to changes in dopamine activity. When these animals were injected with a dopamine agonist (i.e. L-Dopa) brain dopamine activity was stimulated preferentially on the intact side. This resulted in an asymmetrical stimulation of motor activity that was manifested as a turning or rotational behavior. The onset and number of rotations provided a measure of both the time course as well as the extent of increased dopamine activity.

Figure 18:
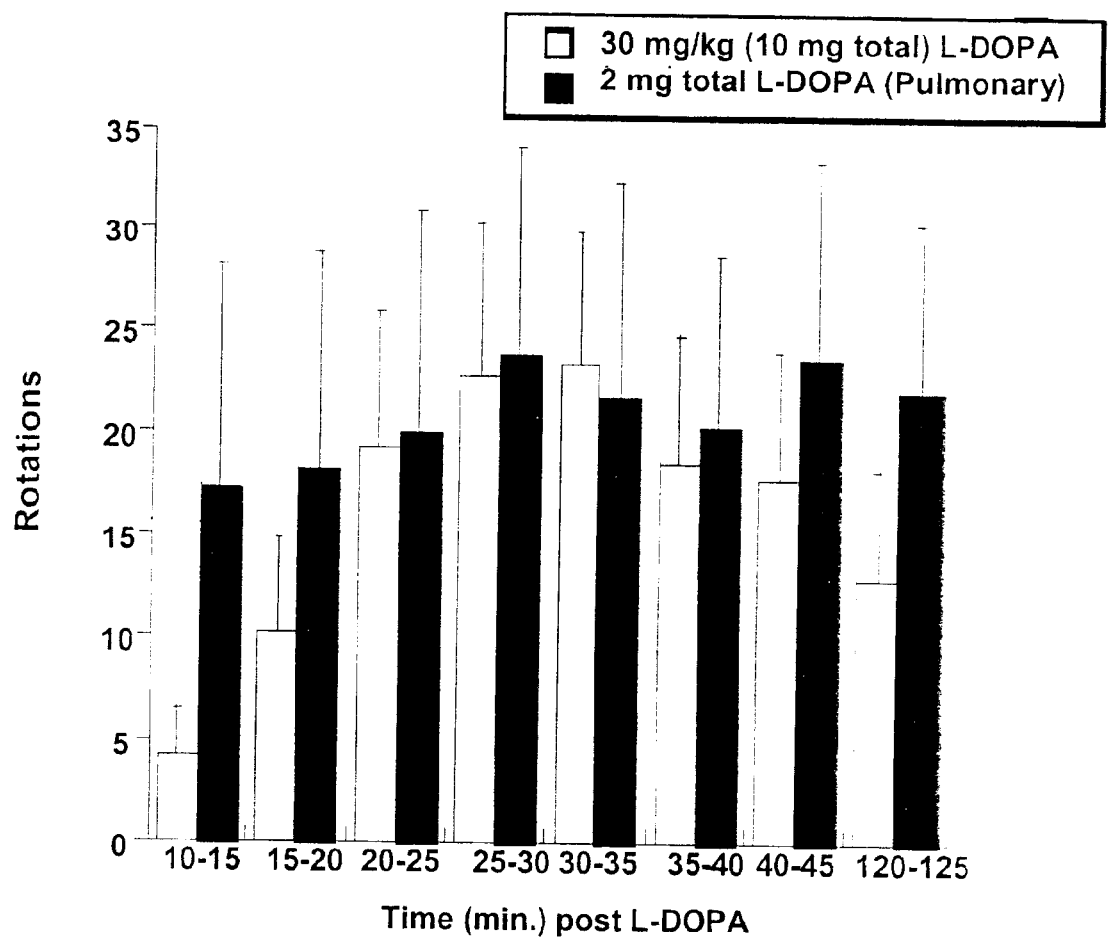

The results are shown in FIG. 18. Oral administration of L-Dopa produced a marked clockwise rotation behavior that was modest during the first 10–15 minutes post L-Dopa administration (<5 rotations/animal). During the next 20 minutes, the number of rotations increased markedly, with peak levels occurring approximately 30 minutes after L-Dopa indicating increased dopamine activity in the intact striatum of the brain. During the next 90 minutes, the number of rotations gradually decreased, but this decrease, relative to peak levels, did not reach statistical significance ($p>0.05$).

In contrast to oral administration, pulmonary delivery of L-Dopa rapidly increased rotation behavior indicating much more rapid conversion of L-Dopa to dopamine in the intact striatum. Rotations in this group were greater than 3 times that produced by oral delivery within the first 10–15 minutes. The numbers of rotations increased slightly, peaked at 25–30 minutes, and remained relatively stable thereafter. While a trend towards increased rotations, relative to oral delivery, was seen 120 minutes after dosing, this did not reach statistical significance ($p > 0.05$). Rotation behavior was virtually eliminated in animals that did not receive pre-treatment with carbidopa (data not shown).

EXAMPLE 8

The pharmacodynamic effects of a pulmonary versus oral benzodiazepine-type drug, alprazolam, were evaluated using a standard pre-clinical test of anxiolytic drug action. In this test, the chemical convulsant pentylenetetrazol (PZT), which is known to produce well characterized seizures in rodents, was administered to rats. The test was selected based on its sensitivity to a wide range of benzodiazapines and to the fact that the relative potency of benzodiazapines in blocking PZT-induced seizures is believed to be similar to the magnitude of their anti-anxiety effects in humans. The ability of alprazolam to block PZT-induced seizures was used as a measure of the pharmacodynamic effects of alprazolm.

Determinations of the anti-anxiolytic activity of alprazolam were made following oral gavage, or insufflation directly into the lungs of rats. Alprazolam (Sigma, St. Louis, Mo. was administered via aerodynamically light particles which included 10% alprazolam, 20% sodium citrate, 10% calcium chloride and 60% DPPC. For oral delivery, alprazolam was suspended in light corn syrup and administered via gavage. For pulmonary delivery, an insufflation technique was used. Animals were briefly anesthetized with isoflurane (1–2%) and a laryngoscope was used to visualize the epiglottis and the blunt-tip insufflation device (PennCentury Insufflation powder delivery device) was inserted into the airway. A bolus of air (3 cc), from an attached syringe, was used to deliver the pre-loaded powder from the chamber of the device into the animals' lungs. The doses for pulmonary delivery were 0 (blank particles that included 20% sodium citrate, 10% calcium chloride and 70% DPPC), 0.088, 0.175, or 0.35 mgs total alprazolam, and the doses for oral delivery were 0, 0.088, 0.175, 0.35, 0.70, 1.75, or 3.50 mgs total alprazolam. These doses were chosen to encompass the range of effective and ineffective oral doses. Accordingly, any potential benefits of pulmonary delivery could be directly compared to the oral dose response curve for alprazolam.

For both oral and pulmonary delivery, alprazolam was administered either 10 or 30 minutes prior to PZT, obtained from Sigma, St. Louis, Mo., (60 mg/kg given i.p). To control for potential interactions between alprazolam and isoflurane, all animals receiving oral alprazolam also received isoflurane immediately following dosing as described above. For all animals, the number of seizures as well as the time to seizure onset and seizure duration was recorded for 45 minutes after administration of PZT. Any animal that did not exhibit seizure activity was assigned the maximum possible time for seizure onset (45 minutes) and the minimal possible time for seizure duration (0 seconds).

Pulmonary delivery of alprazolam produced a rapid and robust decrease in the incidence of seizures, as shown in Table 11. While 80% of control animals (blank particles) exhibited seizures, pulmonary alprazolam produced a robust and dose-related decrease in the number of animals manifesting seizures when administered 10 minutes prior to PZT. With alprazolam doses as low as 0.088 mgs, only 33% of the animals had seizures. With further dose escalation to 0.35 mgs of alprazolam, seizure activity was virtually eliminated with only 13% of the animals exhibiting seizures.

In contrast to the rapid and robust effects of pulmonary alprazolam, the effects of oral delivery were delayed (Table 11). When given 30 minutes prior to PZT, oral alprazolam produced a dose-related decrease in seizures. While only 27% of the animals had seizures following the highest dose tested (0.35 mgs), this same dose of alprazolam was ineffective when administered only 10 minutes prior to PZT (i.e, a dose that was maximally effective when administered by the pulmonary route). These studies also demonstrated that when given 10 minutes prior to PZT, approximately 10 times the oral dose of alprazolam was required to achieve seizure suppression comparable to pulmonary delivery. While only 13% of the animals that received 0.35 mgs of particles including alprazolam had seizures, the oral dose required to produce this effect was 3.50 mgs.

Figure 19A:
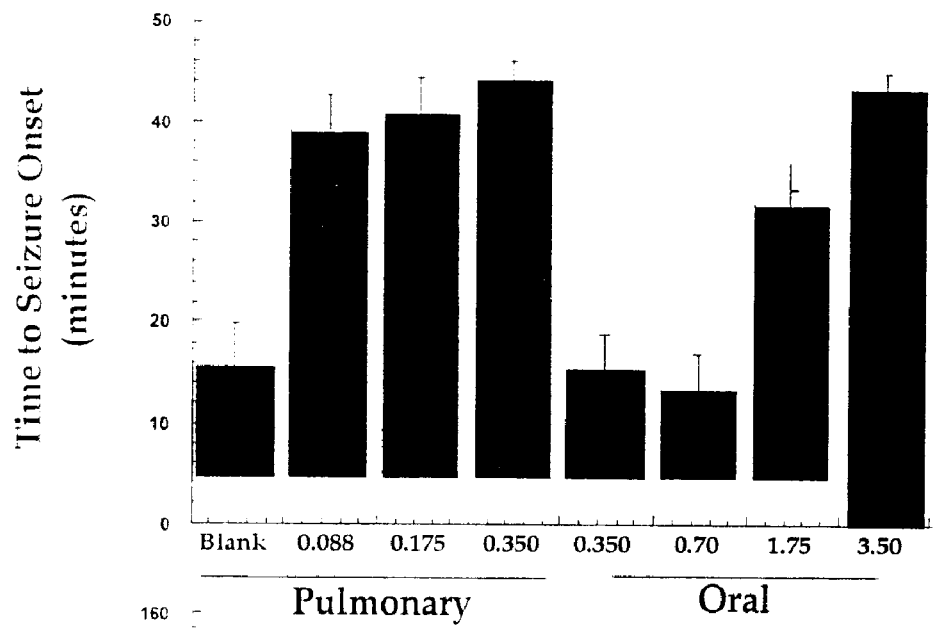

The benefits of pulmonary delivery over oral delivery were also evident when examining the time to seizure onset (Table 11 and FIG. 19A). The effects of oral alprazolam were again delayed relative to pulmonary administration. As shown above, oral delivery was markedly less effective when alprazolam was given 10 minutes versus 30 minutes before PZT. In contrast, all doses of pulmonary alprazolam produced rapid and robust effects when given only 10 minutes prior to PZT. Not only were the effects of pulmonary delivery more rapid, but the effective pulmonary dose was markedly lower than the effective oral dose. For instance, when comparable doses of alprazolam (0.35 mgs) were administered by both the oral and pulmonary routes 10 minutes prior to PZT, pulmonary administration resulted in seizure onset times that were nearly maximal (>42 minutes). Oral administration of the same dose of alprazolam, however, did not increase the latency to seizure onset relative to control animals. In fact, oral alprazolam did not significantly increase the time to seizure onset until the dose was escalated to 1.75 mgs and effects comparable to those obtained with pulmonary delivery required an oral dose that was 10 times higher than the pulmonary dose (0.35 vs 3.50 mgs).

Figure 19B:
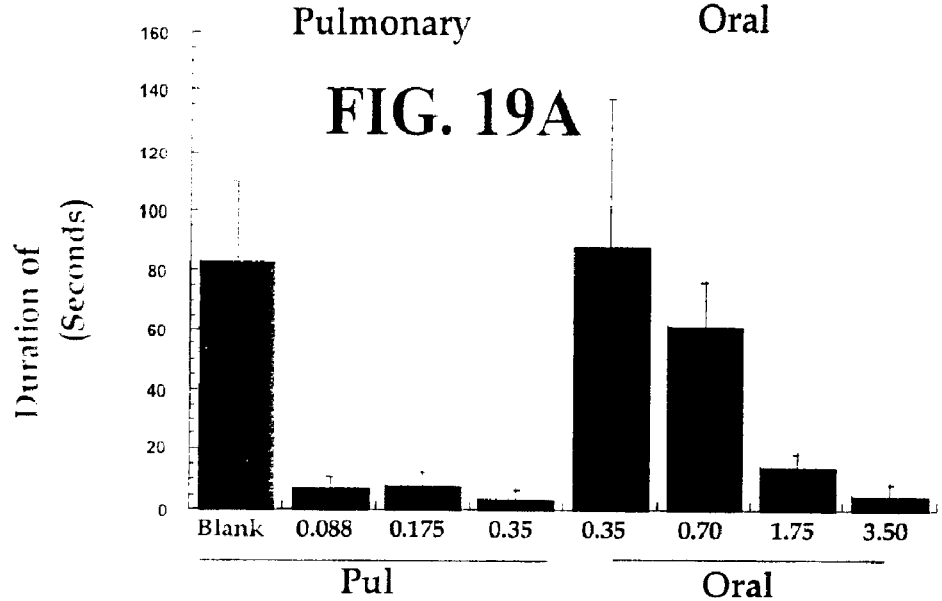

Similar results were also observed when quantifying the effects of the route of alprazolam administration on the duration of the seizure (Table 11 and FIG. 19B). Pulmonary administration exerted a more rapid effect and also required substantially less total drug relative to oral alprazolam. Again, oral delivery was markedly less effective at reducing the duration of seizures when alprazolam was given 10 minutes versus 30 minutes before PZT. Moreover, the maximally effective oral dose, delivered 10 minutes prior to PZT, was 3.50 mgs of alprazolam. In contrast, pulmonary delivery of only 0.088 mgs of alprazolam (nearly 40-fold lower than the maximally effective oral dose) produced a comparable decrease in seizure duration.

Figure 20A:
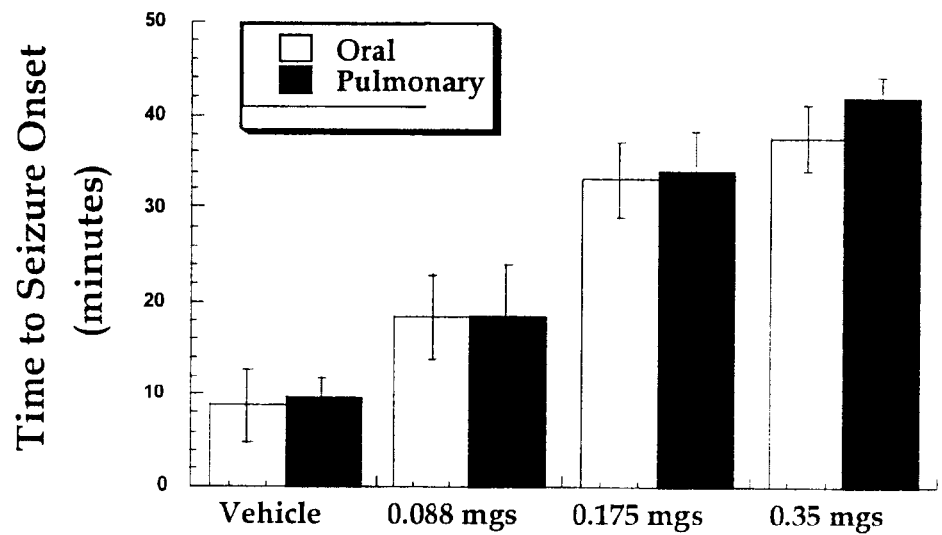
Figure 20B:
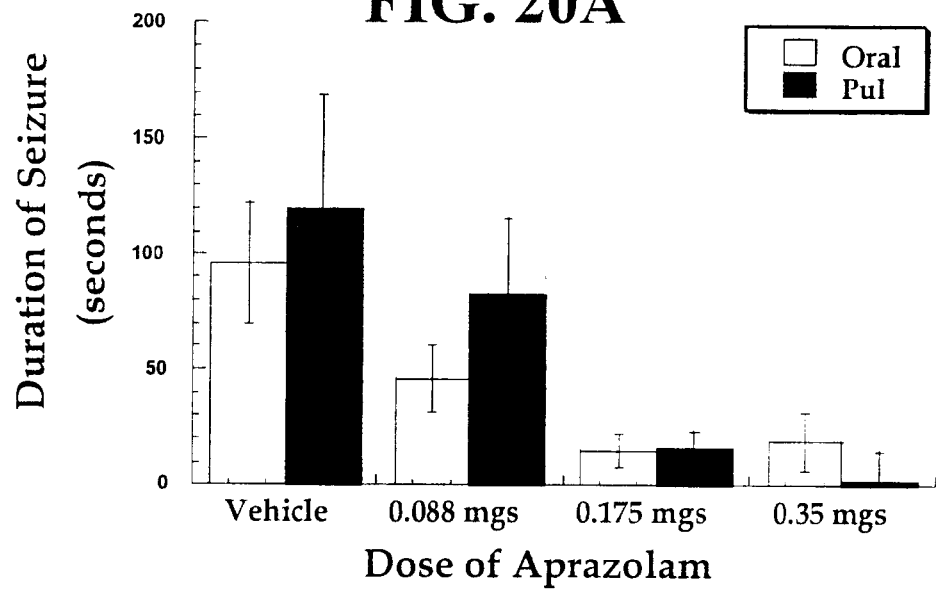

A time course analysis revealed that while the relative advantages of pulmonary over oral alprazolam declined as the interval between alprazolam and PZT was increased, pulmonary delivery remained as effective as oral delivery. While oral alprazolam became increasingly more effective as the interval between alprazolam and PZT treatment increased from 10 to 30 minutes, the effects of pulmonary delivery remained relatively constant over the same time period. In fact, no differences in seizure activity were seen when comparable oral and pulmonary doses of alprazolam were delivered 30 minutes prior to PZT. While a trend towards fewer seizures was seen with pulmonary delivery, these differences were modest and did not reach statistical significance (Table 11B; p>0.05). Moreover, no statistically significant differences were observed between any oral and pulmonary dose when comparing the time to seizure onset or the duration of those seizures (FIGS. 20A and 11B).

Figure 3:
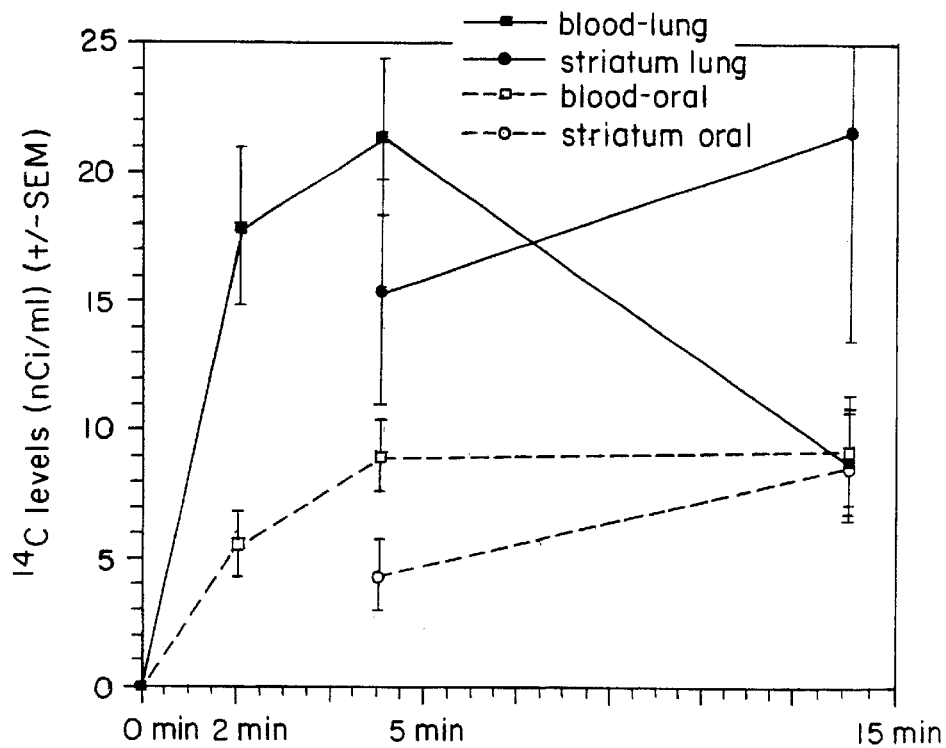
Figure 21A:
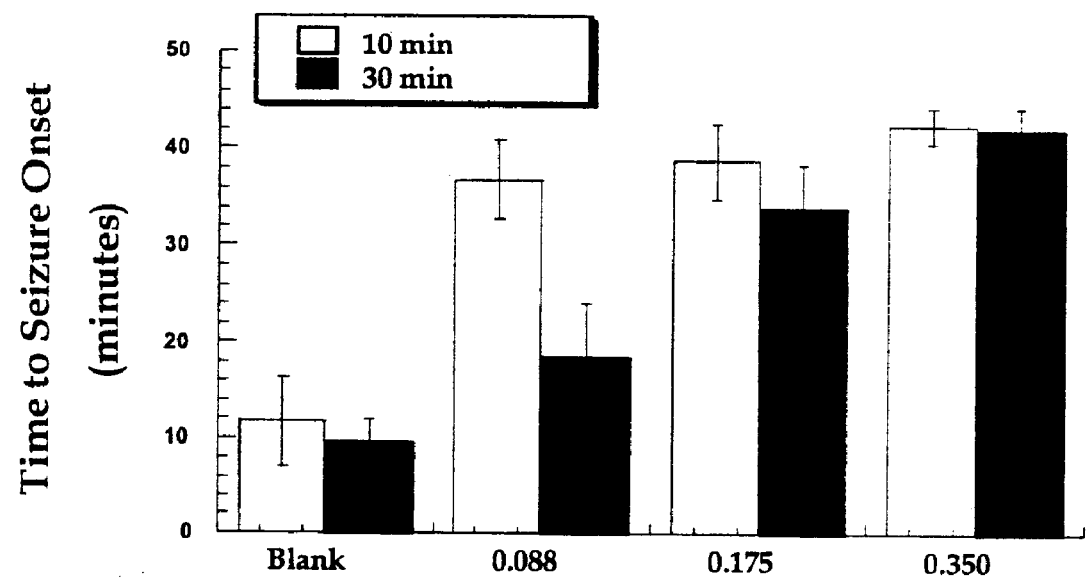
Figure 21B:
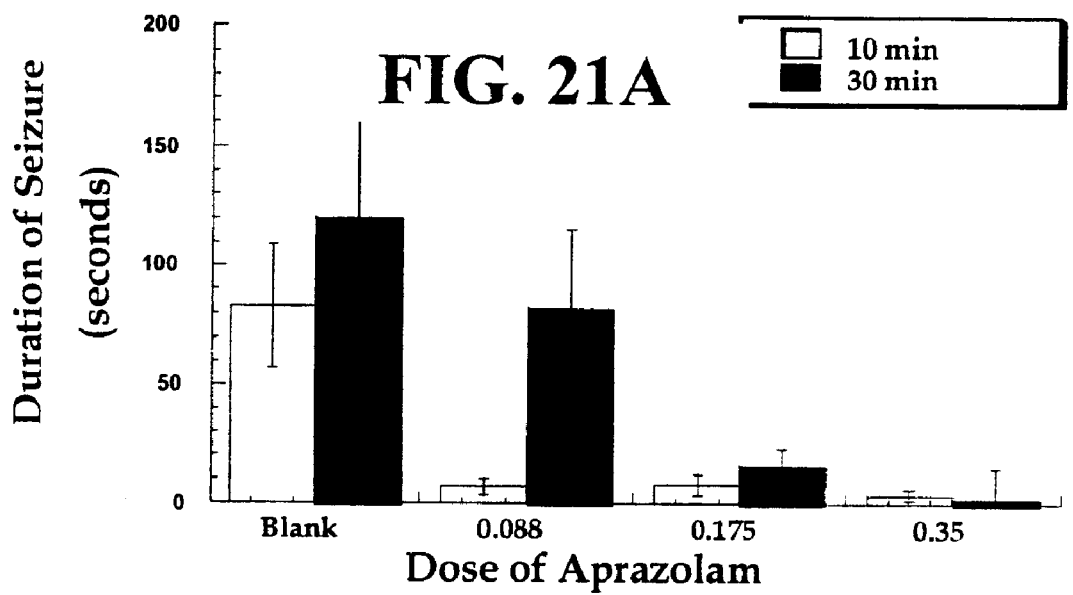

FIGS. 21A and 21B further demonstrate that the effects of pulmonary alprazolam remained relatively constant as the time between alprazolam and PZT treatment increased. Importantly though, a detailed analysis of the results indicated that alprazolam was modestly more effective when the interval between alprazolam and PZT was kept at a minimum. At each dose tested, fewer animals had seizures when alprazolam was delivered 10 minutes vs 30 minutes prior to PZT (although this effect did not reach statistical significance, p>0.05). The benefit of maintaining a close temporal relationship between alprazolam and PZT was also beginning to emerge when examining the time to seizure onset and the duration of seizure activity. While no differences were seen at the higher alprazolam doses (0.175 and 0.35 mgs), animals receiving the lowest dose of alprazolam (0.088 mgs) 10 minutes prior to PZT showed significantly increased times for seizure onset and significantly decreased seizure durations relative to animals treated 30 minutes prior to PZT (FIG. 3).

TABLE 11

Effects of Alprazolam on PZT-Induced Seizures

| Route | Animals With Seizures | | Minutes to Seizure Onset | | Duration of Seizure (seconds) | |
|---|---|---|---|---|---|---|
| Pulmonary | | | | | | |
| 10 minutes prior to PZT | | | | | | |
| Blank | 12/15 | (80%) | 11.72 | (4.63) | 83.0 | (26.04) |
| 0.088 mgs | 5/15 | (33%) | 36.71 | (3.93) | 7.0 | (3.53) |
| 0.175 mgs | 3/15 | (20%) | 38.61 | (3.81) | 8.0 | (4.3) |
| 0.35 mgs | 2/15 | (13%) | 42.28 | (1.98) | 4.0 | (2.60) |
| 30 minutes prior to PZT | | | | | | |
| Blank | 15/15 | (100%) | 9.58 | (2.25) | 120.13 | (49.33) |
| 0.088 mgs | 9/15 | (60%) | 18.47 | (5.50) | 82.67 | (33.0) |
| 0.175 mgs | 5/15 | (33%) | 34.05 | (4.20) | 16.07 | (6.89) |
| 0.35 mgs | 2/15 | (13%) | 41.98 | (2.18) | 2.69 | (1.90) |
| Oral | | | | | | |
| 10 minutes prior to PZT | | | | | | |
| 0.35 mgs | 13/15 | (87%) | 11.49 | (3.80) | 88.0 | (49.22) |
| 0.70 mgs | 13/15 | (87%) | 9.24 | (3.93) | 62.07 | (14.58) |
| 1.75 mgs | 7/15 | (47%) | 29.03 | (4.41) | 14.47 | (4.04) |
| 3.50 mgs | 2/14 | (14%) | 43.37 | (1.52) | 5.40 | (3.47) |
| 30 minutes prior to PZT | | | | | | |
| 0 mgs | 13/15 | (87%) | 8.75 | (3.95) | 96.0 | (26.08) |
| 0.088 mgs | 11/15 | (73%) | 18.38 | (4.55) | 46.0 | (14.48) |
| 0.175 mgs | 7/15 | (47%) | 33.10 | (4.07) | 15.0 | (6.75) |
| 0.35 mgs | 4/15 | (27%) | 37.58 | (3.50) | 19.0 | (12.36) |

Note:
all data presented for time to seizure onset and duration of seizute are presented as mean ± SEM While this invention has been particularly shown and described with references to preferred embodiments thereof, it will be understood by those skilled in the art that various changes in form and details may be made therein without departing from the scope of the invention encompassed by the appended claims.

What is claimed is:

1. A method for treating Parkinson's disease comprising administering to the respiratory tract of a patient in need of treatment or rescue therapy a drug for treating Parkinson's disease wherein the drug is administered in a dose that is at least about two times less than that required by oral administration and wherein delivery is to the pulmonary system.

2. The method of claim 1 wherein the drug is levodopa.

3. The method of claim 1 wherein the dose is between about two times and about five times less than that required by oral administration.

4. The method of claim 1 wherein the dose is between about two times and about ten times less than that required by oral administration.

5. The method of claim 1 wherein delivery is to the alveoli region of the pulmonary system.

6. The method of claim 1 wherein administering is for rescue therapy.

7. The method of claim 1 wherein administering is during ongoing treatment.

8. The method of claim 1 wherein the drug is present in dry powder particles.

9. The method of claim 8 wherein the drug is present in the dry powder particles in an amount of at least 20 weight percent in the drug containing particles.

10. The method of claim 8 wherein the drug is present in the dry powder particles in an amount of at least 40 weight percent in the drug containing particles.

11. The method of claim 8 wherein the drug is present in the dry powder particles in an amount of at least 50 weight percent in the drug containing particles.

12. The method of claim 8 wherein the particles have a tap density of less than about 0.4 g/cm$^3$.

13. The method of claim 8 wherein the particles have a mass median aerodynamic diameter of less than about 5 microns.

14. The method of claim 8 wherein the particles have a mass median geometric diameter greater than about 5 microns.

15. The method of claim 8 wherein the particles have a mass median aerodynamic diameter of less than about 3 microns.

16. The method of claim 8 wherein the particles include a phospholipid.

17. The method of claim 8 wherein the particles include a multivalent salt.

18. The method of claim 8 wherein the particles are administered via a dry powder inhaler.

19. The method of claim 18 wherein the dry powder inhaler is a single dose breath activated dry powder inhaler.

20. The method of claim 1 further comprising co-administering at least one additional agent wherein the drug and the agent are present in the same formulation.

21. The method of claim 1 further comprising co-administering at least one additional agent wherein the drug and the agent are separately formulated.

22. The method of claim 21 wherein the drug and the agent are blended together into a receptacle.

23. The method of claim 21 wherein the drug and the agent are administered sequentially.

24. The method of claim 1 further comprising co-administering at least one additional agent wherein the additional agent is administered by conventional therapies.

* * * * *